(12) United States Patent
Soejima et al.

(10) Patent No.: US 7,575,872 B2
(45) Date of Patent: Aug. 18, 2009

(54) ANTIBODY AGAINST VON WILLEBRAND FACTOR CLEAVING ENZYME AND ASSAY SYSTEM USING THE SAME

(75) Inventors: Kenji Soejima, Kumamoto (JP); Noriko Mimura, Kumamoto (JP); Hiroaki Maeda, Kumamoto (JP); Chikateru Nozaki, Kumamoto (JP); Takayoshi Hamamoto, Kumamoto (JP); Tomohiro Nakagaki, Kumamoto (JP)

(73) Assignee: Juridical Foundation The Chemo-Sero-Therapeutic Research Institute, Kumamoto (JP)

(*) Notice: Subject to any disclaimer, the term of this patent is extended or adjusted under 35 U.S.C. 154(b) by 246 days.

(21) Appl. No.: 10/529,009

(22) PCT Filed: Sep. 25, 2003

(86) PCT No.: PCT/JP03/12280

§ 371 (c)(1),
(2), (4) Date: Mar. 24, 2005

(87) PCT Pub. No.: WO2004/029242

PCT Pub. Date: Apr. 8, 2004

(65) Prior Publication Data

US 2006/0251655 A1 Nov. 9, 2006

(30) Foreign Application Priority Data

Sep. 25, 2002 (JP) .......................... 2002-279924
Dec. 26, 2002 (JP) .......................... 2002-377569

(51) Int. Cl.
*G01N 33/53* (2006.01)
*C12N 5/20* (2006.01)
*C07K 16/00* (2006.01)
*C07K 16/28* (2006.01)

(52) U.S. Cl. ............ 435/7.1; 435/326; 530/387.1; 530/388.1; 530/388.25

(58) Field of Classification Search .................. None
See application file for complete search history.

(56) References Cited

U.S. PATENT DOCUMENTS 7,037,658 B2 * 5/2006 Ginsburg et al. ............... 435/6

FOREIGN PATENT DOCUMENTS

| EP | 1152055 | * | 4/2001 |
| WO | WO 02/04441 A3 | * | 1/2002 |
| WO | WO 02/88366 A1 | | 11/2002 |

OTHER PUBLICATIONS

Chung and Fujikawa. Processing of von Willebrand factor by ADAMTS-13. Biochemistry. Sep. 17, 2002;41(37):11065-70.*

Furlan et al. Partial purification and characterization of a protease from human plasma cleaving von Willebrand factor to fragments produced by in vivo proteolysis. Blood. May 15, 1996;87(10):4223-34.*

Zheng et al. The reference teachings anticipate the claimed invention. "Structure of von Willebrand factor-cleaving protease (ADAMTS13), a RT metalloprotease involved in *Thrombocytopenic purpura.*"*

Campbell A, General properties and applications of monoclonal antibodies, Elsevier Science Publishers, section 1.1, pp. 1-32, 1984.*

Abaza MS, Atassi MZ. Effects of amino acid substitutions outside an antigenic site on protein binding to monoclonal antibodies of predetermined specificity obtained by peptide immunization: demonstration with region 94-100 (antigenic site 3) of myoglobin.. J Protein Chem. Oct. 1992;11(5):433-44.*

Lederman S, et al. A single amino acid substitution in a common African allele of the CD4 molecule ablates binding of the monoclonal antibody, OKT4. Mol Immunol. 28(11):1171-81, 1991.*

Li CH, Yamashiro D, Tseng LF, Chang WC, Ferrara P. beta-Endorphin omission analogs: dissociation of immunoreactivity from other biological activities. Proc Natl Acad Sci U S A. 77(6):3211-3214, 1980.*

Liu et al The AGDV residues on the gamma chain carboxyl terminus of platelet-bound fibrinogen are needed for platelet aggregation. Biochimica et Biophysica Acta 1343:316-326, 1997.*

Y. Fujimura et al., "Von Willebrand factor-cleaving protease and Upshaw-Schulman syndrome", Int. J. Hematol., (Jan. 2002), vol. 75, No. 1, pp. 25-34.

S. Cal et al., "Cloning expression analysis and structural characterization of seven novel human ADAMTSs, a family of metalloproteinases with disintegrin and thrombospondin-1 domains", Gene., Jan. 2002, vol. 283, No. 1-2, pp. 49-62.

DW Chung et al., "Processing of von Willebrand factor by ADAMTS-13", Biochemistry, 2002, vol. 41, No. 37 pp. 11065-11070.

Osama Kanemitsu et al., "Kotai Kogaku Nyumon", Chijinshokan Co., Ltd., Jan. 25, 1994, pp. 195-204, 145-166 and 115-124.

Barbara Plaimauer et al., "Cloning, expression, and functional characterization of the von Willebrand factor-cleaving protease (ADAMTS13)", Blood, Nov. 15, 2002, vol. 100, No. 10, pp. 3626-3632.

(Continued)

*Primary Examiner*—Maher M Haddad
(74) *Attorney, Agent, or Firm*—Stephen A. Bent; Foley & Lardner LLP

(57) ABSTRACT

It is intended to provide an antibody showing immunoreactivity selectively to ADAMTS-13 and applications of this antibody in epitope analysis or diagnosis of an ADAMTS-13 autoantibody-positive patient. Alternatively, it is intended to provide a process for producing and use of a modified ADAMTS-13 molecule partially deleted aiming at the application in pharmaceutical products. An antibody specific for ADAMTS-13 which can be obtained from a warm-blooded animal immunized and sensitized with a polypeptide containing a part or the whole of ADAMTS-13 amino acid sequence; a process for producing an antibody comprising a step of immunizing and sensitizing a warm-blooded animal with a polypeptide containing a part or the whole of ADAMTS-13 amino acid sequence; use of the above-described antibody including a method of detecting and purifying ADAMTS-13; and a modified ADAMTS-13 molecule partially deleted are provided.

8 Claims, 15 Drawing Sheets

OTHER PUBLICATIONS

Han-Mou Tsai et al., "Antibodies to von Willebrand Factor-Cleaving Preotease in Acute Thrombotic *Thrombocytopenic purpura*", The New England Journal of Medicine, vol. 339, No. 22, Nov. 26, 1998, pp. 1585-1594.

Levy et al., "Mutations in a member of the ADAMTS gene family cause thrombotic *Thrombocytopenic purpura*", Nature, vol. 413, Oct. 4, 2001, pp. 488-494.

Xinglong Zheng et al., "Structure of von Willebrand Factor-cleaving Protease (ADAMTS13), a Metalloprotease Involved in Thrombotic *Thrombocytopenic purpura*", The Journal of Biological Chemistry, vol. 276, No. 44, Nov. 2, 2001, pp. 41059-41063.

Helena E. Gerritsen et al., "Partial amino acid sequence of purified von Willebrand factor-cleaving protease", Blood, vol. 98, No. 6, Sep. 15, 2001, pp. 1654-1661.

Koichi Kokame et al., "Mutations and common polymorphisms in ADAMTS13 gene responsible for von Willebrand factor-cleaving protease activity", PNAS, vol. 99, No. 18, pp. 11902-11907, Sep. 3, 2002.

\* cited by examiner

1. Gel filtration sample of FI paste of human pooled plasma
2. Plasma 1 from healthy subject
3. Plasma 2 from healthy subject
4. Plasma 3 from healthy subject
5. Plasma 1 from TTP patient
6. Plasma 2 from TTP patient

Fig. 12

(MoAb-PoAb system)

1. Allow each reagent to be warmed to room temperature
2. Add a sample to WH10 MoAb immobilized plate by 100 μL/well
   37°C, 1 hour
3. Wash the plate with 0.05% Tween-20-TBS three times
4. Dilute PoAb 1 or PoAb 2 with a diluting solution (1% BSA-TBS) so that it may become
   1 μg/ml and add to the plate by 100 μL/well
   37°C, 1 hour
5. Wash the plate with 0.05% Tween-20-TBS three times
6. Dilute an anti-rabbit IgG-HRP labelled conjugate with a diluting solution (1% BSA-TBS)
   to 10000-fold and add to the plate by 100 μL/well
   37°C, 1 hour
7. Wash the plate with 0.05% Tween-20-TBS three times
8. Add a TMB substrate solution (prepared by mixing two liquids at room temperature
   immediately before use) to the plate by 100 μL/well (positive well turns blue); about 10
   minutes (so that the color of 100 ng/ml of the recombinant product enclosed as a standard
   may be finally about 1 as OD450 nm after the reaction is terminated) at room temperature
   (positive well turns yellow)
9. Add a reaction terminating liquid (0.5 M sulfuric acid) to the plate by 100 μL/well
10. Measure the plate with a plate reader at 450 nm and 650 nm

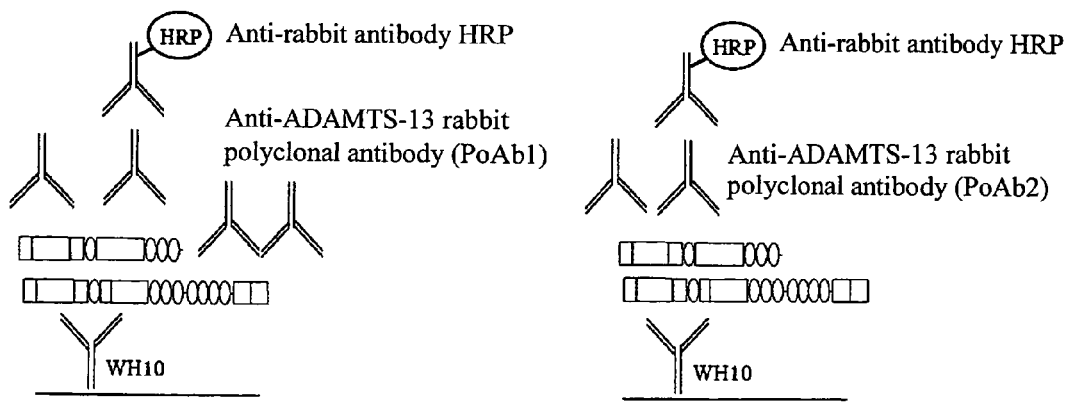

Fig. 14

(MoAb-MoAb system)

1. Allow each reagent to be warmed to room temperature
2. Add a sample to WH10 MoAb immobilized plate by 100 μL/well
   37°C, 1 hour
3. Wash the plate with 0.05% Tween-20-TBS three times
4. Dilute a biotinylated antibody with a diluting solution (1% BSA-TBS) so that it may become
   1 μg/ml and add to the plate by 100 μL/well
   37°C, 1 hour
5. Wash the plate with 0.05% Tween-20-TBS three times
6. Dilute a streptavidin-HRP labelled conjugate with a diluting solution (1% BSA-TBS)
   to 10000-fold and add to the plate by 100 μL/well
   37°C, 1 hour
7. Wash the plate with 0.05% Tween-20-TBS three times
8. Add a TMB substrate solution (prepared by mixing two liquids at room temperature
   immediately before use) to the plate by 100 μL/well (positive well turns blue); about 10
   minutes (so that the color of 100 ng/ml of the recombinant product enclosed as a standard
   may be finally about 1 as OD450 nm after the reaction is terminated) at room temperature
   (positive well turns yellow)
9. Add a reaction terminating liquid (0.5 M sulfuric acid) to the plate by 100 μL/well
10. Measure the plate    with a plate reader at 450 nm and 650 nm.

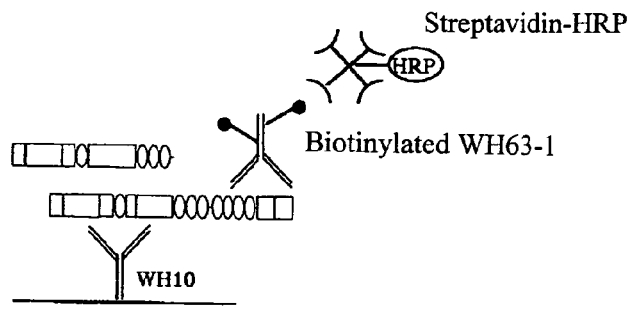

Fig. 17

1. ADAMTS-13 solution: normal rabbit serum = 1:1
2. ADAMTS-13 solution: normal rabbit serum (diluted 5-fold)= 1:1
3. ADAMTS-13 solution: peptide immunized rabbit serum = 1:1
4. ADAMTS-13 solution: peptide immunized rabbit serum (diluted 5-fold)= 1:1
5. ADAMTS-13 solution: recombinant protein immunized rabbit serum = 1:1
6. ADAMTS-13 solution: recombinant protein immunized rabbit serum (diluted 5-fold)= 1:1
7. ADAMTS-13 solution: 10 mM EDTA = 1:1
8. ADAMTS-13 solution: buffer only = 1:1
9. Buffer (without ADAMTS-13): buffer = 1:1

ANTIBODY AGAINST VON WILLEBRAND FACTOR CLEAVING ENZYME AND ASSAY SYSTEM USING THE SAME

TECHNICAL FIELD

The present invention relates to a protein in the field of the ethical drugs. Specifically, the present invention relates to a full-length or partial fragment of a cleaving enzyme (hereinafter also referred to as ADAMTS-13) specific for von Willebrand factor (von Willebrand Factor: hereinafter also referred to as vWF) which participates in blood coagulation and an antibody against them. The antibody against ADAMTS-13 provided by the present invention opens a possibility of effectively preparing the enzyme of high purity for use in the diagnosis of deficit and decrease of the enzyme such as in thrombotic thrombocytopenic purpura (hereinafter also referred to as TTP) or the diagnosis of an autoantibody-positive patient to this enzyme protein, and replacement therapy of the enzyme for a patient suffering from a disease associated therewith. In another respect, it enables discrimination between decrease of platelets due to disseminated intravascular coagulation (hereinafter also abbreviated as DIC) and the like and decrease of platelets due to congenital or acquired TTP and provides an index at the time of platelet injection. In addition, use as a novel anti-ADAMTS-13 drug can be envisaged.

BACKGROUND ART

The vWF is a blood coagulation factor which is produced by vascular endothelial cells or bone marrow megakaryocytes and is present as a multimer structure (molecular weight 500 to 20,000 kDa) composed of subunits of a single type each having 2,050 amino-acid residue (monomer about 250 kDa) and bound by S—S bond. The blood concentration is about 10 μg/ml, and generally one with higher molecular weight has a higher specific activity.

The vWF has two major functions as a blood coagulation factor; one is a function as a career protein to bind to and stabilize blood coagulation factor VIII and the other is a function to allow blood platelets to adhere and aggregate to the tissue beneath vascular endothelial cells at damaged vascular wall and to form a platelet thrombus.

Thrombotic thrombocytopenic purpura (TTP) is a disease which forms platelet thrombus in body tissue arterioles and capillary vessels throughout the body, and the mortality related to this disease increased by about 3 times in 1971 through 1991 in spite of progress of recent medical technology. Pathologically, TTP is considered to be caused by disorder of vascular endothelial cells and platelet aggregation in blood vessels, and immunohistologically significant amount of vWF is observed in the formed platelet thrombus, and it is supposed that vWF plays an important role in the origin thereof. The multimer structure of vWF in the patient with TTP shows primacy of normal or high molecular vWF, and particularly, unusually large vWF multimer (ULvWFM) usually not observed and large vWF multimer (LvWFM) are presumed to play an important role in promotion of platelet aggregation and microthrombus formation under high shear stress. In the meantime, it has been known that vWF is decomposed at the position of 842Tyr-843Met by the action of vWF cleaving enzyme (vWF-cleaving protease) in the circulating blood in healthy people under high shear stress. Therefore, as for TTP, a scenario is assumed in which the activity of the above-mentioned enzyme in plasma is lowered by some cause, ULvWFM to LvWFM increase to enhance platelet aggregation, thereby causing platelet thrombus formation in the blood vessel.

The gene encoding vWF cleaving enzyme which is the main part of the activity having this enzyme activity, also known as ADAMTS-13, was cloned by the applicant of this application in 2001 (WO 02/088366). The knowledge about the molecular structure of ADAMTS-13 is summarized below.

As for the domain composition of ADAMTS-13, propeptide is present following the signal peptide and subsequently, RQRR (SEQ ID NO: 21) sequence of cleavage motif of Furin is present and a metalloprotease domain which contains a reprolysin type zinc chelate region consisting of a consensus sequence of HEXXHXXGXXHD (SEQ ID NO: 22) follows (to P285stop). And via a disintegrin-like domain which is found in snake venom metalloprotease (to W387stop), it connects to the first Tsp1 motif (Tsp1-1) consisting of about 50 to 60 residues which is generally considered to be important for molecule recognition (to Q449stop) and further continues to Gys-rich region in which RGDS (SEQ ID NO: 23) sequence, one of cell adhesion motifs, is included (to T581stop). Subsequently, via a spacer domain which consists of about 130 amino acid residues containing no cysteine residue (to W688stop), additional seven Tsp1 motifs (Tsp1-2 to 8) follows again, and CUB domain-1 and -2 continue which are known to be first found in complement component C1r or C1s.

In the meantime, there has not been established an efficient and high-purity purification process for this enzyme nor a method for qualitative and/or quantitive diagnosis on the amount of existence of this enzyme. Furthermore, no method for diagnosing an autoantibody-positive patient to this enzyme has been established, and the domain essential for expression of the activity of this enzyme has not been identified.

DISCLOSURE OF THE INVENTION

Under the circumstances, the first object of the present invention is to provide an antibody which is immunoreactive to ADAMTS-13 with high selectivity.

The second object of the present invention is to provide a process for preparing this antibody.

The third object of the present invention is to provide applications of this antibody.

The fourth object of the present invention is to provide a full-length or partially deleted ADAMTS-13 molecule which enables to identify the existence or recognition region of the above-mentioned antibody or an antibody derived from an autoantibody-positive patient.

The fifth object of the present invention is to provide a process for preparing such a full-length or modified molecule.

The sixth object of the present invention is to provide applications of this full-length or modified molecule.

As an approach to therapy of a patient suffering from congenital absence of specific vWF cleaving enzyme as well as a postnatally antibody-positive patient to this enzyme, plasma exchange treatment is performed till now and establishment of replacement treatment with a pure enzyme such as a purified product or a recombinant of the enzyme is desired. It is reported that a patient with familial TTP congenitally lacks specific vWF cleaving enzyme and that non-familial TTP is postnatally caused by production of an autoantibody to the enzyme. Therefore, replacement treatment with this enzyme is desirable for a familial TTP patient (actually plasma administration is performed) whereas removal of autoantibody and supplement of this enzyme by plasma exchange are required for a non-familial case.

Accordingly, an efficient preparing process or diagnosis of this enzyme etc. is needed but sufficient purity and yield are not expectable for the vWF cleaving enzyme by a process in which the enzyme is purified from the plasma or supernatant of expressing recombinant according to the process described in a former application (WO 02/088366) by the present applicant or other methods (see, for example, Kokame, K. et al., "Proc. N. A. S. USA", 2002, vol. 99, pp. 11902-11907; Fujikawa, K. et al., "Blood", 2001, vol. 98, pp. 1662-1666). In addition, technique for measuring the amount of this enzyme, particularly the amount of the enzyme as an amount of antigen has not existed until now. Moreover, in case of thrombocytopenia, there have been risks such as exacerbation of conditions by blood platelet injection when the conditions are not caused by DIC but by TTP as a primary disease.

Therefore, the present invention aims at providing an antibody against vWF cleaving enzyme for solving these problems. This antibody enables quantification and purification of vWF.

Under the above-mentioned situation, the present inventors have conducted intensive studies to achieve isolation and identification of vWF cleaving enzyme and as a result we have succeeded in purification and isolation of the desired vWF cleaving enzyme which has not been reported yet and have come to identify the amino acid sequence of the matured protein and the gene which encodes the amino acid sequence (WO 02/088366).

For the purpose of identifying the region considered to be essential for expressing activity, we then prepared modified molecules in which successive deletion was caused from the C-terminus side CUB domain and measured the vWF cleaving activity. It was confirmed from this study that the enzyme activity was qualitatively maintained even in a molecule which consists of amino acids from the vicinity of 688th to the N-terminus in SEQ ID No. 1, which is called spacer domain. On the other hand, it was confirmed that normal secretion was prevented in a molecule consisting of amino acids up to the vicinity of the 581st and that secretion into culture supernatant was observed but the enzyme activity was weak or not observed in a molecule consisting of amino acids up to the vicinity of the 449th, and these findings indicated the domain essential to activation of the enzyme molecule of the present invention. Thus the preparation of the epitope region necessary for preparing an antibody which can neutralize the activity of this enzyme or an antibody which can detect the present enzyme molecule having activity was enabled.

Peptide prepared based on the amino acid sequence of ADAMTS-13 obtained and the like can be used as an antigen to prepare monoclonal and polyclonal antibody, etc. according to a usual immunizing method (Current Protocols in Molecular Biology, Edited by F. M. Ausbel et al. (1987), Antibody Engineering: A PRACTICAL APPROACH Edited by J. McCAFFERTY et al. (1996), Antibodies: A Laboratory Mannual, Edited by Harlow David Lane (1988) or ANTIBODY ENGINEERING, second edition, Edited by Carl A. K. BORREBAECK (1995)). Alternatively, the antibody which binds the above-mentioned protein can be produced by antigen preparing technique utilizing phage display technology (Phage Display of Peptides and Proteins: A Laboratory Manual Edited by Brian K. Kay et al. (1996), Antibody Engineering: A PRACTICAL APPROACH Edited by J. McCAFFERTY et al. (1996), or ANTIBODY ENGINEERING second edition edited by Carl A. K. BORREBAECK (1995)). Alternatively, isolation of a neutralization antibody or a simple binding antibody to the activity of this enzyme from the sample of a TTP patient who is autoantibody-positive against the activity of this enzyme is also possible based on these technologies. And the use of these antibodies enables applications to the diagnosis and treatment of a disease accompanied by change of the amount of this enzyme, for example, TTP etc. Alternatively, the thus prepared antibody can be used for preparing an antibody against mouse ADAMTS-13, for example, and an autoantibody-positive model mouse can be created by introducing the antibody into a mouse or by introducing an expression vector having a gene of this antibody incorporated therein into a mouse.

That is, the present invention is as follows.

[1] An antibody against a protein or peptide, wherein the protein or peptide consists of a full-length amino acid sequence constituting a von Willebrand factor specific cleaving enzyme (hereinafter also referred to as ADAMTS-13), a modified amino acid sequence thereof in which one or several amino acids thereof are deleted, substituted or added or a partial sequence of any one of the above-mentioned amino acid sequences, or a polypeptide chain comprising the above-mentioned full-length amino acid sequence;

[2] The antibody according to [1] wherein the ADAMTS-13 is derived from a primate or rodents;

[3] An antibody against a protein, wherein the protein consists of a modified amino acid sequence in which one or more amino acids of the amino acid sequence constituting ADAMTS-13 represented by SEQ ID No. 1 are deleted, substituted or added or a partial sequence of any one of the above-mentioned amino acid sequences, or a polypeptide chain comprising the above-mentioned amino acid sequence of ADAMTS-13;

[4] An antibody recognizing a portion of the polypeptide of the amino acid sequence constituting ADAMTS-13 represented by SEQ ID No. 1, wherein said portion is a range from the spacer domain to the N-terminus, or from the metalloprotease domain, disintegrin-like domain, Tsp1-1 domain or Cys-rich region to the spacer domain;

[5] The antibody according to any one of [1] to [4] applicable to affinity purification of a protein, wherein the protein consists of a modified amino acid sequence in which one or several amino acids of the amino acid sequence constituting ADAMTS-13 are deleted, substituted or added or a partial sequence of any one of the above-mentioned amino acid sequences, or a polypeptide chain comprising the above-mentioned amino acid sequence of ADAMTS-13;

[6] The antibody according to any one of [1] to [4] capable of inhibiting or neutralizing the enzyme activity of a protein, wherein the protein consists of a modified amino acid sequence in which one or several amino acids of the amino acid sequence constituting ADAMTS-13 are deleted, substituted or added or a partial sequence of any one of the above-mentioned amino acid sequences, or a polypeptide chain comprising the above-mentioned amino acid sequence of ADAMTS-13;

[7] The antibody according to [6], wherein the antibody recognizes the range from the spacer domain to the N-terminus, the metalloprotease domain or the disintegrin-like domain of ADAMTS-13;

[8] An antibody prepared by an immunogen comprising a partial peptide of ADAMTS-13 of SEQ ID Nos. 2 and 3;

[9] An antibody prepared by immunizing with a polypeptide chain expressed as a full-length or partial-length of SEQ ID No. 1 or by transfecting an expression vector capable of expressing the polypeptide chain directly into an animal;

[10] The antibody according to any one of [1] to [9] which is a polyclonal antibody;

[11] The antibody according to any one of [1] to [9] which is a monoclonal antibody and a gene encoding said antibody;

[12] The monoclonal antibody according to [9] which is an antibody produced by a hybridoma selected from the group consisting of hybridomas WH10, WH63.1, WHS40.3, Pep4-34.1, WH2-22-1A, WH2-1-1, WH2-11-1, Pep6-6A and Pep4-5B-1 and a gene encoding the monoclonal antibody wherein WH10, WH63.1, WHS40.3 and Pep4-34.1 were deposited at Patent Microorganisms Depositary, National Institute of Advanced Industrial Science and Technology (AIST), an Independent Administrative Institution (Tsukuba Central 6, 1-1-1 Higashi, Tsukuba, Ibaraki, Japan) under accession numbers FERM BP-8174, FERM BP-8175, FERM BP-8176 and FERM BP-8177 respectively on Sep. 4, 2002, and WH2-22-1A, WH2-1-1, WH2-11-1, Pep6-6A and Pep4-5B-1 were deposited at International Patent Organism Depositary, National Institute of Advanced Industrial Science and Technology (AIST), an Independent Administrative Institution (Tsukuba Central 6, 1-1-1 Higashi, Tsukuba, Ibaraki, Japan) under accession numbers FERM BP-8483, FERM BP-8484, FERM BP-8485, FERM BP-8474 and FERM BP-8475 respectively on Apr. 22, 2003 and Sep. 10, 2003;

[13] An antibody which can bind to or competitively bind to an epitope of ADAMTS-13 recognized by an antibody according to any one of [1] to [12];

[14] A pharmaceutical composition or diagnostic medicine comprising an antibody according to any one of [1] to [13];

[15] A labelled protein comprising an antibody according to any one of [1] to [13] as a component;

[16] An isolated cell which can produce an antibody according to any one of [1] to [13];

[17] The cell according to [16] which is a hybridoma;

[18] The cell according to [17] selected from the group consisting of hybridoma line WH10 (accession number FERM BP-8174), hybridoma line WH63.1 (accession number FERM BP-8175), hybridoma line WHS40.3 (accession number FERM BP-8176), hybridoma line Pep4-34.1 (accession number FERM BP-8177), hybridoma line WH2-22-1A (accession number FERM BP-8483), hybridoma line WH2-1-1 (accession number FERM BP-8484), hybridoma line WH2-11-1 (accession number FERM BP-8485), hybridoma line Pep6-6A (accession number FERM BP-8474) and hybridoma line Pep4-5B-1 (accession number FERM BP-8475);

[19] An immunoassay kit comprising an antibody according to any one of [1] to [13];

[20] A process for preparing an antibody comprising the steps of immunizing and sensitizing a warm-blooded animal with a polypeptide comprising a part or the whole of the amino acid sequence of ADAMTS-13, and extracting an antibody according to any one of [1] to [13] from the humor of said warm-blooded immunized and sensitized animal;

[21] The process for preparing an antibody according to [20] wherein the polypeptide for immunizing and sensitizing a warm-blooded animal comprises a part or the whole of the amino acid sequence represented by SEQ ID No. 1 in the sequence list as a part of ADAMTS-13;

[22] A process for preparing an antibody comprising the steps of culturing in vivo or in vitro an isolated cell which can produce an antibody according to any one of [1] to [13], and extracting said antibody from the humor or culture;

[23] The process for preparing an antibody according to [22] wherein the isolated cell which can produce an antibody is a hybridoma;

[24] The process for preparing an antibody according to any one of [20] to [23] wherein the antibody is extracted by a purification method including one or more selected from the group consisting of salting out, dialysis, filtration, concentration, centrifugation, fractional precipitation, gel filtration chromatography, ion exchange chromatography, high-performance liquid chromatography, affinity chromatography, gel electrophoresis and isoelectric focusing;

[25] A detection method of ADAMTS-13 characterized by contacting an antibody according to any one of [1] to [13] with a sample to be tested and detecting ADAMTS-13 by immunoreaction;

[26] The detection method according to [25] which is carried out by radioimmunoassay, enzyme immunoassay or fluoroimmunoassay using an antibody according to any one of [1] to [13];

[27] The detection method according to [25] or [26] wherein the sample to be tested is a biological sample extracted from a living body;

[28] A process for purifying ADAMTS-13 comprising the steps of contacting an antibody according to any one of [1] to [13] with a mixture containing ADAMTS-13 and impurities to adsorb said protein on the antibody and desorbing said adsorbed protein from the antibody;

[29] The purification method according to [28] wherein the antibody is bound to a water insoluble carrier;

[30] A diagnostic medicine or pharmaceutical product which comprises as a main component the full-length sequence or a partially deleted variant of ADAMTS-13;

[31] The diagnostic medicine or pharmaceutical product according to [30] comprising as a main component a region from the spacer domain of ADAMTS-13 to the N-terminus, or from the metalloprotease domain, disintegrin-like domain, Tsp1-1 domain or Cys-rich region to the spacer domain;

[32] A reagent, diagnostic medicine or pharmaceutical product for detecting an antibody against the polypeptide chain comprising as a main component the full-length sequence or a partially deleted variant of ADAMTS-13; and

[33] Use and a preparation method of an antigen for detecting an antibody or analyzing an epitope comprising as a main component the full-length sequence or a partially deleted variant of ADAMTS-13.

An antibody which can bind to ADAMTS-13 is disclosed here. These antibodies can be modified using standard technology in the art. Antibodies similar to the antibody illustrated here first can be also prepared by combining a method disclosed here and a known method. These methods of generating an antibody include immunizing a mammal (for example, mouse, rat, rabbit, horse, goat, sheep or monkey) with ADAMTS-13 or a fragment thereof or transfecting an expression vector which can recombinantly express ADAMTS-13 subcutaneously, intracutaneously or intramuscularly. The antibody can be obtained from the immunized animal using various techniques known in the art, and can be preferably screened using binding of the antibody to an antigen of interest. Isolation of the antibody and/or antibody generating cell from the animal can be achieved by a step of slaughtering the animal.

Alternatively or in addition to immunizing a mammal with ADAMTS-13, a specific antibody against ADAMTS-13 can be obtained from a recombinantly generated library of variable domain of the expressed immunoglobulin using, for example, a lambda bacteriophage or a bacteriophage filament showing a functional immunoglobulin binding domain on the surface. The library may be a natural one constructed from a sequence obtained from an organism which has not been immunized by any ADAMTS-13 (or fragmentation) or may be constructed from a sequence obtained from an organism which has been exposed to an antigen of interest.

The monoclonal antibody used here can be prepared by the method first described by Kohler and Milstein, Nature, 256: 495, 1975, or a recombination method (see Mage and Lamoyi, Monoclonal Antibody Production Techniques and Applications, pp. 79-97, Marcel Dekker, New York, 1987).

In the hybridoma method, in order to derive lymphocytes which produce or can produce an antibody specifically binding to ADAMTS-13 used for immunization, a suitable host warm-blooded animal such as mouse, rat, rabbit, horse, goat, sheep or monkey is immunized with an antigen in a subcutaneous, intraperitoneal or intramuscular route. Alternatively, lymphocytes can be immunized in vitro. Subsequently, the lymphocyte is fused with a myeloma cell using a suitable fusing agent, for example, polyethylene glycol etc. to form a hybridoma cell [see Goding, Monoclonal antibodies: Principles and Practice, pp. 59-103 (Academic Press, 1986)].

The antigens used for immunization include a natural ADAMTS-13 isolated from the blood of a human or non-human manual and a recombinant ADAMTS-13 prepared by using the genetic engineering technique, and may be derived from human or other mammals. Not only a full-length ADAMTS-13 but also an enzymatically cleaved fragment or a partial peptide of a recombinant ADAMTS-13 genetically engineered from a fragment of DNA which encodes the ADAMTS-13 can be used. Examples of the fragment of ADAMTS-13 include a fragment containing a region from the spacer domain to the N-terminus, metalloprotease domain, disintegrin-like domain, Tsp1-1 domain or Cys-rich region to the spacer domain.

The thus prepared hybridoma cells can be seeded and cultured in a suitable culture medium containing preferably one or more substances which inhibit replication or survival of un-fused parent myeloma cells. For example, when the parent myeloma cells lack an enzyme hypoxanthine-guanine phosphoribosyl transferase (HGPRT or HPRT), the medium for culturing hybridomas typically contains hypoxanthine, aminopterin, and thymidine (HAT culture medium) and these substances inhibit replication of HGPRT deficit cells.

Preferable myeloma cells are those which effectively fuse and support stable and high-level antibody expression by the selected antibody generation cells and have susceptibility to culture media such as HAT culture medium.

The culture medium for culturing hybridoma cells may be assayed based on the generation of monoclonal antibody against ADAMTS-13. Preferably, specific binding is measured by solid phase enzyme-linked immunosorbent assay (ELISA). The monoclonal antibody of the present invention specifically binds to ADAMTS-13 or a partial fragment thereof.

The epitope to which the antibody binds can be mapped by allowing the ADAMTS-13 molecules of C-terminal deletion variant described below to be expressed. Therefore, the present invention encompasses an antibody which can bind to the ADAMTS-13 epitope to which the illustrated antibody binds.

In a preferable embodiment of the present invention, the monoclonal antibody may have a larger affinity surpassing micromole, or a larger affinity (i.e., larger affinity than $10^{-6}$ mol) when measured by, for example, Scatchard analysis (see Munson, Pollard, Anal. Biochem. 107:220, 1980).

After identifying the hybridoma cell which produces the antibody having desired specificity and affinity, the clones are subcloned of the clone by limiting dilution, and cultured by a standard method. The culture medium suitable for this purpose includes Dulbecco's modified Eagle culture medium or RPMI-1640 culture medium. Furthermore, the hybridoma cell can be proliferated in vivo as an ascitic tumor in an animal.

By culturing the hybridoma cell in vitro, culture supernatant containing a desired antibody can be obtained. In addition, ascites containing a desired antibody can be obtained by transplanting this hybridoma to abdominal cavity of a mammal such as a mouse.

The monoclonal antibody secreted by the hybridoma is preferably separated from the culture medium, ascitic fluid or serum by a conventional immunoglobulin purification process, for example, with protein A Sepharose, hydroxylapatite chromatography, gel electrophoresis, dialysis or affinity chromatography.

The nucleic acid which encodes the monoclonal antibody of the present invention can be easily isolated and sequenced by a known method in the art, for example, using an oligonucleotide probe which can specifically bind to the gene encoding heavy and light chains of a rodent antibody. The hybridoma cell of the present invention is a preferable source of supply of the nucleic acid which encodes the antibodies or the fragments thereof. After being isolated, the nucleic acid can be ligated to an expression vector or a cloning vector, then transformed into a host cell, and the recombinant host cells is cultured so that the grown cells can produce the monoclonal antibody.

The hybridoma which can produce the antibody which has desired binding characteristics contains the nucleic acid which encodes the antibody (including antibody fragments) and as a host cell which can express these fall within the limits of the present invention. In addition, the present invention provides a method for producing an antibody comprising culturing the cells which can produce the antibody under the condition that they produce and preferably secret the antibody.

The antibody of the present invention can be modified by various methods. Furthermore, the term "antibody" should be interpreted as covering all the binding substances that have a binding domain which shows the specificity needed. Therefore, the present invention covers the antigen or epitope, antibody fragment containing a synthetic molecule and a molecule having a similar form to an antibody which can bind to ADAMTS-13 here, derivatives and functional equivalents and homologues of the antibody.

The examples of the antibody fragment which can bind to the antigen or other binding pair are Fab fragment which consists of VL, VH, C1 and CH1 domains; Fd fragment which consists of VH and CH1 domains; Fv fragment which consists of VL and VH domains of a single arm of the antibody; dAb fragment which consists of VH domain; and a divalent fragment containing isolated CDR domain and F(ab')$_2$ fragment and two Fab fragments connected by a disulfide bridge in the hinge domain. A single chain Fv fragment is also contained.

The hybridoma which produces the monoclonal antibody of the present invention can be subjected to genetic variation or other variation. Furthermore, it will be understood by those skilled in the art that the monoclonal antibody can be subjected to the technology of the recombination DNA technology for producing the other antibody, humanized antibody or chimera molecule maintaining the specificity of the original antibody. Such a technology can include introducing a DNA which encodes the variable domain or complementarity determination region (CDR) of immunoglobulin of the antibody into the constant domain or a constant domain connected to a framework region of another immunoglobulin.

The hybridomas which produce the monoclonal antibody provided by the present invention include WH10, WH63.1, WH540.3, Pep4-34.1, WH2-22-1A, WH2-1-1, WH2-11-1, Pep6-6A and Pep4-5B-1.

Immunoassay

The antibodies of the present invention can be used in various assay forms for detecting or diagnostic method of the present invention. The antibody can be used as a binding agent which can specifically binds to ADAMTS-13, and for example, enables to detect the ADAMTS-13 in the sample in vitro. In another aspect, it can be used as a developing agent after contacted to the analysis target for determining the fraction of the binding site of the binding agent occupied with the vWF cleaving enzyme, which is the analyte in the analysis target (the analysis target). That is, the antibody of the present invention binds to the analysis target at the binding site and by measuring the amount of the antibody of the present invention bound to the analysis target, the amount of the analysis target can also be determined and thus the antibody of the present invention can be used as if it were a developing agent which clarifies the existence of the analyte.

Use of the antibody, particularly use of the antibody as a developing agent in assay includes labelling them with a labeling substance or a reporter molecule which can directly or indirectly yield a detectable and preferably measurable signal. In addition, the antibody of the present invention also includes a labelled antibody. Labelling can be performed by coupling a labeling substance or a reporter molecule with the antibody and this coupling can be formed directly or indirectly, for example, through a covalent bonding via a peptide bond or a non-covalent bonding. The coupling via a peptide bond can be obtained by recombination expression of a fused gene which encodes the antibody and reporter molecule. Any of the methods known in the art to separately bind the antibody to detectable parts can be used including methods described in Hunter et al., Nature, 144:945, 1962; David et al., Biochemistry 13:1014, 1974; Pain et al., J. Immunol. Meth. 40:219, 1981; and Nygren, J. Histochem and Cytochem. 30:407, 1982.

The labeling substances or reporter molecules include fluorescent dyes, fluorophores or laser dyes, etc., which have spectroscopically isolated absorption or luminescence and these can be coupled with the antibody by the covalent bond. The suitable fluorescent dyes include fluorescein, rhodamine, luciferin, phycoerythrin and Texas Red. The suitable coloring dyes include diaminobenzidine. The other detectable labels include radioisotope labels, for example, $^{3}H$, $^{14}C$, $^{32}P$, $^{35}S$, $^{125}I$, or $^{99m}Tc$, and enzyme labels which catalyze the reaction bringing about a detectable reaction product and can amplify the signal, for example, alkaline phosphatase, β-galactosidase or a horseradish peroxidase. The labelling of these enzyme can be performed using a technology known in the art including those using biotin/avidin or biotin/streptavidin binding.

The other reporter molecules include particulate materials such as colored polymer colloid particles or, for example, latex beads which can directly or indirectly bring about a detectable signal which can be visually observed, electrically detected or recorded by other means. In addition, magnetic or paramagnetic particles can also be used. Furthermore, the reporter molecule may be an enzyme which catalyzes, for example, a coloring reaction, a discoloration reaction or a reaction changing an electrical property. These may have molecular reactivity which generates characteristic spectral absorption or luminescence by electric transition between energy states. Furthermore, these can include a chemical entity which is used in combination with a biosensor.

Furthermore, since the antibody can bind to ADAMTS-13 specifically more preferentially than to other substances present in the sample, the antibody can be used as a binding agent. Preferably, the binding agent is immobilized so that it can be easily handled in the assay on a solid support, for example, at a specific site. The immobilization can be performed by using a technology known in the art such as physical adsorption or chemical adsorption and biotin/avidin or biotin/streptavidin can be used for example, for chemically binding the antibody onto the solid-state support material (solid support). Typically, the binding reagent and the sample are contacted under suitable conditions so that ADAMTS-13 present in the sample can bind to a binding agent. Subsequently, the occupation ratio of the fraction of the binding site of the binding agent can be measured using a developing agent. That is, the amount of the analysis target can be measured by measuring the amount of the antibody bound to the analysis target in the sample.

When using the antibody of the present invention as the above-mentioned developing agent, the developing agent is labelled (with for example, a radioactive label, a fluorescent label, or an enzyme label) so that it can be detected using a technology known in the art. Accordingly, the radioactive label can be detected using a scintillation counter or other radioactivity counting device, the fluorescent label can be detected using a laser or confocal microscope, and the enzyme label can be detected using an action of the enzyme label on the substrate, typically an action which causes change of color. The developing agent can be used in the competitive method in which the developing agent competes with the analyte for the occupancy binding site of the binding agent or in the non-competitive method in which a labelled developing agent binds to the analyte which has bound to the binding agent or the occupancy binding site. By either of the methods, the fraction of the binding site occupied by the analyte is shown, and, thereby, the analyte concentration in the sample is shown as compared with, for example, the standard obtained by using a sample containing the known concentration of the analyte.

Diagnostic assay is performed using the biological sample from a patient. These samples can also be directly used without pre-treatment, or may be subjected to a treatment such as for removing substances in the sample which may cause interference by, for example, centrifugation or filtration prior to performing the assay. The examples of the suitable biological sample include blood, urine, sweat, tissue or extracted liquid thereof, or serum.

In an embodiment, the present invention relates to a method of diagnosing whether the patient having a risk of TTP or TTP-like diseases or thrombosis dependent on vWF (thrombosis caused by vWF) is suffering from these diseases or estimating the risk or evaluating whether there is any risk of suffering from these diseases, and this process comprises the following steps: (a) contacting a biological sample obtained from a patient with a solid-state support material having thereon an immobilized antibody which can specifically bind to ADAMTS-13; (b) contacting the solid-state support material having thereon an immobilized antibody and with which the sample has been contacted with a labelled developing agent which can bind to unoccupied binding sites of the antibody, bound ADAMTS-13 which has bound to the antibody or occupied binding sites of the antibody; and (c) detecting the label of the developing agent specifically bound in the step (b) in order to obtain the value corresponding to the concentration of ADAMTS-13 in the sample.

In a further embodiment, the present invention provides a method for carrying out diagnosis relating to the vWF-dependent thrombus in a patient, and this method comprises the following: (a) contacting a biological sample obtained from a patient with an anti-ADAMTS-13 antibody according to any one of the claims; and (b) measuring a binding of ADAMTS-13 in the sample to an anti-ADAMTS-13 antibody.

And the process further comprises a step of correlating the value which corresponds to the ADAMTS-13 concentration in the sample to a value obtained from a known standard, for example, steps of performing measurement of a standard having a known concentration, creating a standard curve, and comparing the observed value obtained by the measurement of the substance having an unknown concentration to the standard curve thereby calculating the concentration.

The antibody of the present invention can be used in all of the well-known immunology-measuring methods, for example, competitive binding assay, direct and indirect sandwich assay and immunoprecipitation assay [see Zola, Monoclonal Antibodies: A Manual of Techniques, pp. 147-158 (CRC Press, 1987)].

Sandwich assay uses two kinds of antibodies which can bind to different immune sites or epitopes of ADAMTS-13 to be detected respectively. After binding the analyte of the analysis target to the primary antibody immobilized on the solid-state support material, a secondary antibody is allowed to bind to the analyte to form an insoluble three part complex (antigen, primary antibody and secondary antibody) in the sandwich assay. The secondary antibody can be labelled in the detectable moiety (labelled substance or reporter molecule) or can be measured by using an anti-immunoglobulin antibody which has been labelled in a detectable moiety (indirect sandwich assay). For example, one model of sandwich assay is ELISA assay whose detectable moiety is an enzyme.

An immunoassay kit containing the antibody of the present invention is also included by the present invention. When the kit is based on an enzyme immunoassay, the kit may comprise an carrier on which the antibody has been solid phased or the antibody may be bound to the carrier beforehand. When this kit is based on the condensing method using carriers such as latex, the kit may comprise carriers on which the antibody is adsorbed. The kit may also comprise a standard sample, blocking solution, reaction solution, reaction terminating liquid, reagents for processing the sample etc. suitably.

The antibody of the present invention is useful in in-vivo imaging, in which the antibody is labelled with a detectable moiety such as a radioisotope, administered to the host, preferably into a blood flow, and the existence and localization in the host of the labelled antibody are measured. The antibody can bind to a tissue or an organ, etc. in which ADAMTS-13 is present or localized. The antibody can be labelled at all portions detectable by nuclear magnetic resonance, X ray fluoroscopy, or other detection means well-known in the art, and by using a specific detection means in accordance with the detectable moiety, the existence and localization of the labelled antibody can be measured, i.e., the existence and localization of ADAMTS-13 can be detected.

Moreover, the antibody of the present invention is also useful as a reagent for affinity purification in affinity chromatography. In this method, the antibody is immobilized on a support such as synthetic resin such as Cellulofine, and filter paper by using a method well-known in the art. Subsequently, after contacting a sample containing ADAMTS-13 to be purified with an immobilized antibody, the support is washed with a solvent which can completely remove all the substances in the sample other than ADAMTS-13 binding to the immobilized antibody. Finally, the support is washed with a solvent which can liberate ADAMTS-13 from the antibody, for example, glycine buffer solution, pH 3 to 5 and the ADAMTS-13 can be isolated and purified.

The antibody of the present invention or ADAMTS-13 molecule or a variant thereof can be blended into a pharmacological composition. That is, the present invention includes a pharmacological composition including the antibody of the present invention or ADAMTS-13 molecule or a variant thereof. Here, a variant is a molecule in which one or more amino acids are deleted, substituted or added in the amino acid sequence of a fragment containing a portion which exhibits a pharmacological effect in the whole molecule or the amino acid sequence of ADAMTS-13 molecule (it is not necessarily a modification maintaining the activity).

The antibody of the present invention contains an antibody which can inhibit or neutralize the enzyme activity which ADAMTS-13 has. Preferably, such an antibody recognizes and binds to the epitope which exists from the spacer domain to the N-terminus in the domain structure of ADAMTS-13. The antibody also recognizes and binds to the epitope which exists in metalloprotease domain, disintegrin-like domain, Tsp1-1 domain, or Cys-Spacer region.

A pharmacological composition can contain pharmacologically acceptable excipient, carrier, buffer solution, stabilizer, or the other substances well-known in the art in addition to the above-mentioned antibody, ADAMTS-13 molecule or a variant thereof. Such a substance is nonpoisonous and does not interfere in the effect of the active ingredients. The strict properties of the carrier or the other substances depend on the administration route, for example, oral, intravenous, intracutaneous or subcutaneous, transnasal, intramuscular or subcutaneously, intraperitoneal route, and suitable ones can be selected according to the administration route.

The pharmacological composition for oral administration can be a tablet, a capsule, powder or liquid form. The tablet can contain solid-type carriers such as gelatin or adjuvant. The pharmacological composition of a liquid type can usually be a carrier, for example, water, petroleum, animal oil, vegetable oil, mineral oil, or synthetic oil. A saline, glucose or other saccharide solution, or glycol, for example, ethylene glycol, propylene glycol or polyethylene glycol is included.

In the case of intravenous, intracutaneous or subcutaneous injection, or the injection to a pain part, the active ingredients may not contain any pyrogenic factor and may be in the form of an aqueous solution which can be parenterally accepted and have a suitable pH, isotonicity and stability. Those skilled in the art can prepare a suitable solution using the medium of isotonicity, for example, sodium chloride liquid, Ringer's solution, lactated Ringer's solution, etc. An antiseptic, a stabilizer, a buffer solution, an antioxidant, and/or other additive agents can be contained if needed.

The antibody against ADAMTS-13 of the present invention, ADAMTS-13 molecule, or a variant thereof can be diluted and formulated with a saline, buffer solution, etc. to prepare a pharmaceutical composition. pH of the preparation is preferably a pH of weak acidity to neutral region near the pH of humor, and preferably 5.0 to 6.4 at the lowest and preferably pH 6.4 to 8.0 at the highest. It can also be provided in the form which can be stored for an extended period of time such as in a freeze-drying form etc., and in this case, it can be dissolved and used with water, saline, buffer solution, etc. at the time of use so that it may become desired concentration. The preparation of the present invention may contain pharmaceutically accepted additives usually used for medicines (for example, carrier, excipient, dilution agent, etc.), stabilization agent, or pharmacologically necessary ingredients. As a stabilization agent, monosaccharides such as glucose, disaccharides such as saccharose and maltose, sugar alcohols such as mannitol and sorbitol, neutral salts such as sodium chloride, amino acids such as glycine, nonionic surfactants such as polyethylene glycol, polyoxyethylene-polyoxypropylene copolymer (Pluronic), polyoxyethylene sorbitan fatty acid ester (Tween), human albumin, etc. can be exemplified, and about 1 to 10 w/v % is preferably added.

The pharmaceutical composition of the present invention can be administered in an effective amount by intravenous injection, intramuscular injection, subcutaneous injection, etc., and is administered at one time or several times. The amount to be administered varies with condition, age, weight, etc., but 0.001 mg to 100 mg per time is preferable.

This specification incorporates the contents disclosed by the specification and/or drawings of Japanese Patent Application Nos. 2002-279924 and 2002-377569, which are the basis of the priority claimed of the present application.

BRIEF DESCRIPTION OF THE DRAWINGS

FIG. 12 is a schematic view of an ELISA system constructed by combining a polyclonal antibody and a monoclonal antibody and a flow chart of the assay;

FIG. 14 is a schematic view of an ELISA system constructed by combining a monoclonal antibody and a monoclonal antibody and a flow chart of the assay;

FIG. 17 shows evaluation of neutralizing ability using the antibody (SDS-PAGE of the vWF cleaving activity under non-reducing conditions);

BEST MODE FOR CARRYING OUT THE INVENTION

Figure 1:
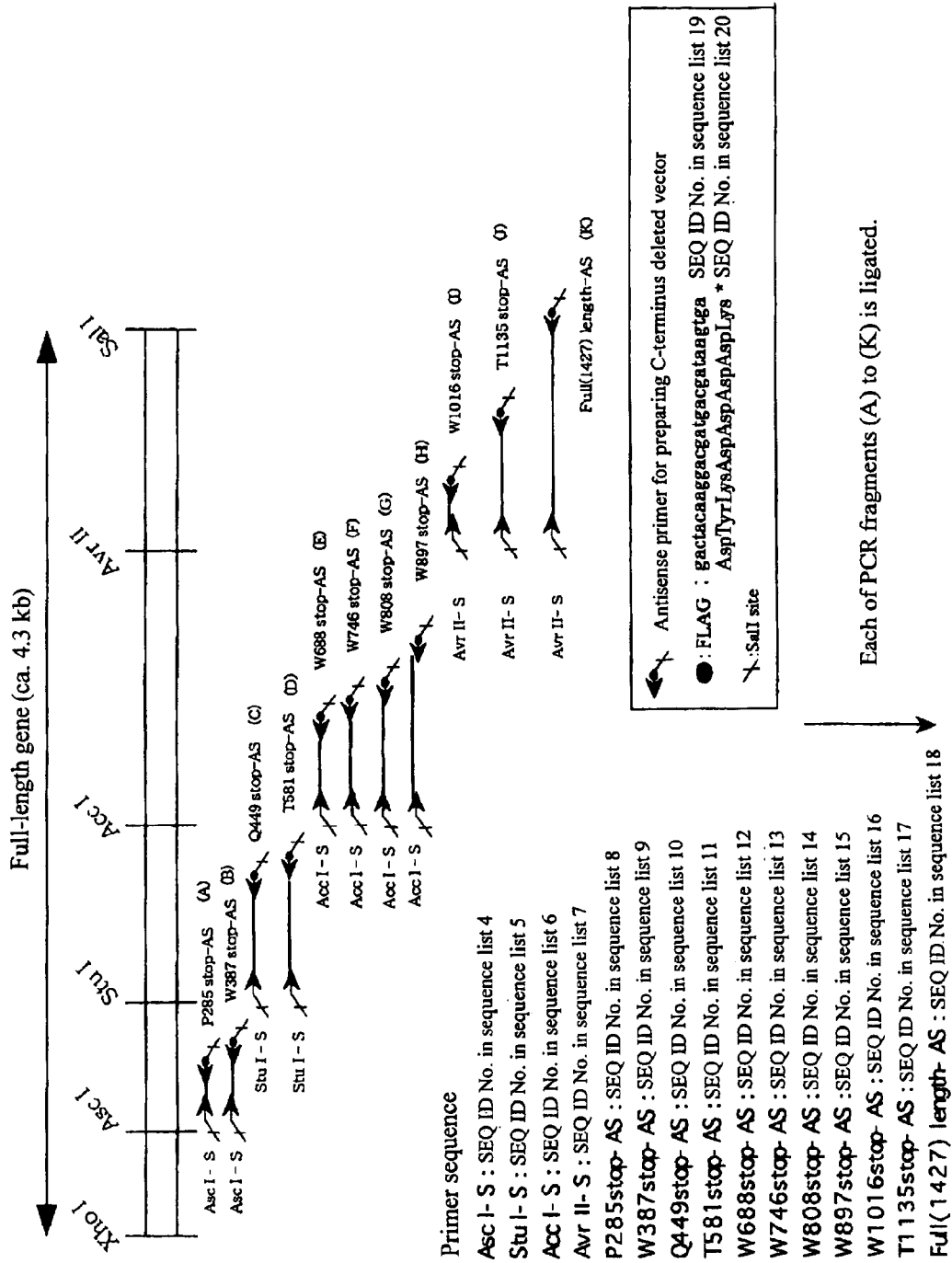
FIG. 1 shows a process for preparing a C-terminal deletion variant for determining the epitope of the antibody.

The present invention will be described in full detail below by way of Examples but the present invention is not limited to these Examples by any means.

EXAMPLE 1

Preparation of Polyclonal Antibodies (PoAb)

Antigen proteins partially purified from human plasma, or synthetic peptides having a part of the amino acid sequence (exemplified by peptides of SEQ ID No. 2 or SEQ ID No. 3) bound to a suitable career substance (KLH etc.)(those appended with Cys to N- or C-terminus in order to facilitate KLH addition), or an expression vector into which was introduced a recombinant protein or a gene encoding the recombinant protein were transfected to a mouse or a rabbit subcutaneously, intradermically or intramuscularly according to a conventional method (Current Protocols in Molecular Biology: Chapter 11 immunology, Antibody Engineering: A PRACTICAL APPROACH Edited by J. McCAFFERTY et al. or ANTIBODY ENGINEERING second edition Edited by Carl A. K. BORREBAECK etc.) to establish a monoclonal antibody expression hybridoma and create polyclonal antibodies (PoAb). As for PoAb, three types, i.e., PoAb1, PoAb2 and PoAb3, were prepared by the transfection of vectors which express full-length, Q449stop or P285stop described below.

EXAMPLE 2

Production of Monoclonal Antibody (MoAb)

Balb/c mice immunized with recombinantly derived ADAMTS-13 and peptides of SEQ ID No. 2 or SEQ ID No. 3 using KLH as a career to the hind leg as a first immunization in the presence of Freund's complete adjuvant were prepared. ADAMTS-13 may be prepared by the method described in WO 02/088366.

One week after inoculating an amount from 1 μg to 10 μg equivalent of the prepared antigen once, cells were sampled from the femoral lymph node of the hind leg or spleen of the mice according to a conventional method. Cells obtained from two mice were mixed with myeloma cell P3X63Ag8U.1 (P3U1)(ATCC accession number CRL-1597: Curr. Top. Microbiol. Immunol., vol. 81, p. 1 (1978)) respectively at a ratio of 1 to 1-2 cells, centrifuged (1,500 rpm, 5 minutes) to remove the supernatant and the precipitated cell lump was loosened enough, and 1 ml of polyethylene glycol solution (45% polyethylene glycol 4000, 55% RPMI culture medium) warmed at 37° C. beforehand was added under agitation. After carrying out incubation at 37° C. for 5 minutes, RPMI culture medium was slowly added so that the whole amount of the liquid might be 50 ml. After centrifugation (1,300 rpm, 7 minutes), the supernatant was removed and the cells were gently loosened. 50 ml of S-Clone CM-B culture medium (product of Sanko Junyaku Co., Ltd.) was added to this, and the cells were gently suspended using a measuring pipette. 100 μl of this cell suspension was put in each well of 4 or 5 of 96-well cell culture plates, and cultured in a $CO_2$ incubator containing 5% carbon dioxide at 37° C. Next day, 100 μl of HAT culture medium (S-Clone CM-B culture medium supplemented with $1\times10^{-4}$ M of hypoxanthine, $1.5\times10^{-3}$ M of thymidine and $4\times10^{-7}$ M of aminopterin) was put in each well, and cultured in a $CO_2$ incubator containing 5% carbon dioxide at 37° C. The medium was substituted with HT culture medium (the above-mentioned HAT culture medium except that aminopterin was removed) for the colonies in which hybridoma was grown enough, a part of the culture supernatant was sampled, and the target hybridoma was separated by the screening method described below.

Separation of the target hybridoma was carried out combining the following ELISA method and the Western blotting method.

(1) ELISA Method

The synthetic peptide antigen prepared in the similar manner as above or a purified antigen (protein concentration: 0.5 to 2 μg/ml) was added to a 96-well micro test plate by 50 μl/well, and immobilized by carrying out incubation at 4° C. overnight. Furthermore, 300 μl of 1% BSA (bovine serum albumin) solution was added, and incubation was carried out in a similar manner to effect masking. To the thus prepared antigen immobilized plate, culture supernatant of a hybridoma obtained by cell fusion method and a hybridoma after cloning were added, and incubated at 4° C. for one hour, and then the plates were washed with TBS three times, and 100 μl/well of a peroxidase-labelled anti-mouse immunoglobulin antibody solution (product of Cappel, 5,000-fold diluted) was added. After incubated at 4° C. for one hour, they were washed with TBS three times and then a TMBZ substrate solution was added to develop the color by a conventional method, and the absorption was measured at the wavelength of 450 nm. In this way, the hybridoma clone which reacts with a purified antigen was selected. This method can be also applied to detecting an autoantibody of ADAMTS-13 in human plasma.

(2) Western Blotting Method

Screening was performed on the positive colony obtained by ELISA by Western blotting method. The purified antigen was subjected to electrophoresis using 8% of SDS-polyacrylamide gel, transferred onto a PVDF membrane, and the membrane was cut into 0.4 to 0.5 cm width. Each small piece was immersed in the hybridoma culture supernatant, and incubated at 37° C. for 1 hour. Then, after washed with TBST (containing 0.05% Tween) three times, they were incubated at 37° C. for 1 hour in a 1:2000 diluted solution of alkaline phosphatase labelled anti-mouse IgG (product of TAGO Inc.). After washed with TBST three times, they were made to develop the color with a coloring reagent (product of Bio-Rad) using BCIP/NBT, and the hybridomas which show the coloring band of the purified antigen were selected and cloned. The hybridoma clones after cloning were sorted in the same technique. About 30 clones of hybridoma which produce the desired monoclonal antibody were obtained by the above-mentioned sorting method. This method was also applicable to the detection of autoantibody against ADAMTS-13 in human plasma.

EXAMPLE 3

Production of C-terminal Deletion Variant of ADAMTS-13

By the strategy shown in FIG. 1 utilizing the full-length vWF cleaving enzyme gene cloning vector (pCR2.1vWFCP), genes expressing the variants in which domains were deleted one by one from the C-terminus (Full 1427stop, T1135stop, W1016stop, W897stop, W808stop, W746stop, W688stop, T581stop, Q449stop, W387stop, P285stop: wherein each number shows the number of amino acid residues from Met encoded by the start codon ATG to the termination codon, showing the site to which the FLAG epitope was appended (DNA sequence: gactacaaggacgatgacgataagtga (SEQ ID No. 19 in the sequence list), amino acid sequence: Asp Tyr Lys Asp Asp Asp Asp Lys (SEQ ID No. 20 in the sequence list))) were prepared using primers of the full-length and SEQ ID Nos. 4 to 18 in the sequence list, and incorporated into the pCAG expression vector (Niwa, H., et al. Gene vol. 108, 193-199), and transfection was carried out in the following procedures using the Hela cell.

Full length ADAMTS-13 gene harbouring vector (pCR2.1vWFCP) of full-length can be obtained by the method described in WO 02/088366.

Figure 2:
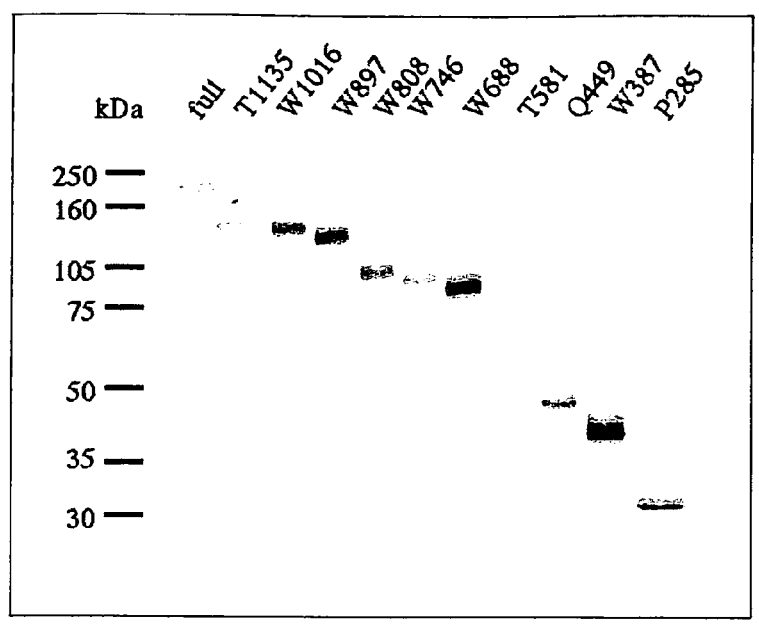
FIG. 2 demonstrates a transient expression of the prepared C-terminal deletion variant by Western blotting under non-reducing conditions using an anti-FLAG antibody.

First, cells were seeded at $1\text{-}3\times10^5$ cells/35 mm dish, and the next day, the above-mentioned expression vector was added by 2 μg to 10 μl of TransIT (product of TAKARA) which is a polyamine transfection reagent and added to 200 μl of serum-free culture medium such as Opti-MEM, and a complex with DNA was prepared according to the instructions appended to the reagent, dropped onto the above-mentioned various cells prepared, incubated for 6 hours, and then incubated at 37° C. for 72 hours after the culture medium was changed to ASF104 serum-free culture medium (product of Ajinomoto Co., Inc.) and the supernatant was collected. Detection was performed by Western blotting method using an anti-FLAG-M2 antibody (product of KODAK), dyed in an anti-mouse Ig-alkaline phosphatase enzyme labelling antibody system (the result demonstrating the observed expression is shown in FIG. 2). This group of modified molecules had an added FLAG tag, and was able to be purified easily using anti-FLAG tag antibody-immobilized agarose which is a conventional method.

EXAMPLE 4

Confirmation of vWF Cleaving Activity of C-terminal Deletion Variant of ADAMTS-13

Preparation of vWF vWF was prepared by subjecting 2 g of plasma cryo fraction dissolved in 20 mL of buffer (0.01% Tween-80/50 mM Tris-HCl/100 mM NaCl pH 7.4) to gel filtration on 2.6×90 cm column of Sephacryl S-500HR (Amersham-Pharmacia)(see WO 02/088366).

vWF Cleaving Reaction

Assay of vWF cleaving activity was performed by the method of WO 02/088366. That is, a sample to which barium chloride was added in a final concentration of 10 mM was pre-incubated at 37° C. for 5 minutes to activate the protease. A buffer (1.5 M Urea/5 mM Tris-HCl pH 8.0 of 15 to 20 mL) was put into a 50 mL falcon tube. Next, membrane filter (0.025 μm) manufactured by Millipore Corp. was allowed to float, and 100 μL of an activated sample to which 50 μL of vWF substrate solution had been added and mixed was added. It was allowed to stand still in an incubator at 37° C. overnight, and the sample was collected from the filter on the next day. The collected sample was evaluated based on the cleaving pattern of vWF shown in the following SDS-PAGE section.

SDS-PAGE

SDS-5% polyacrylamide gel was prepared in house and used. The sample for electrophoresis was 10 μL of the sample described in the section of vWF cleaving activity assay with 2 μL of SDS electrophoresis buffer (in the presence or absence of a reducing agent 2-mercaptoethanol) boiled for 3 minutes. After carrying out electrophoresis at 30 mA for 1 hour, the gel was dyed with Gel Code Blue Stain Reagent (PIERCE).

Figure 3:
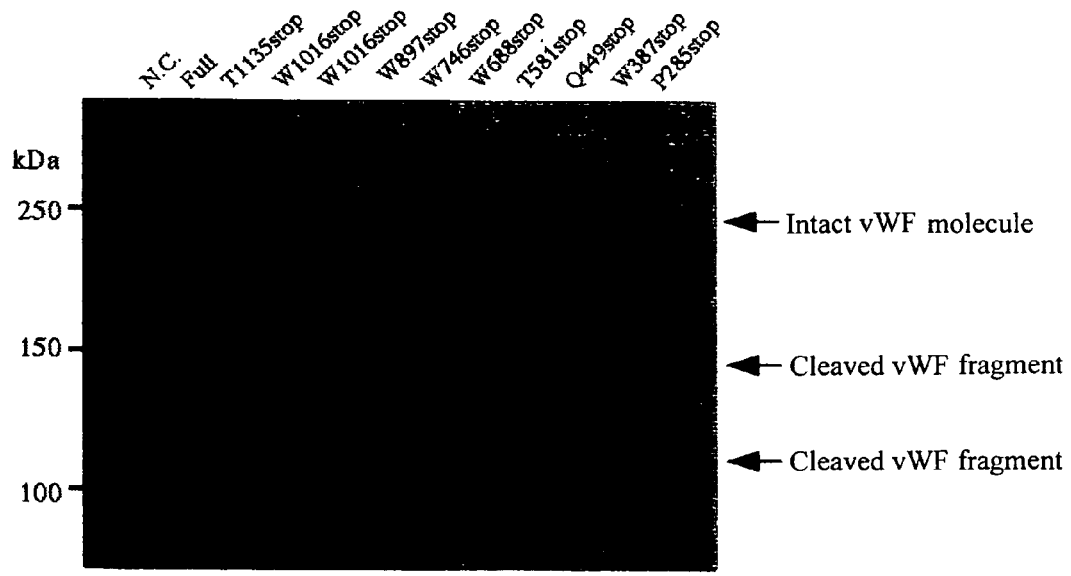
FIG. 3 demonstrates a transiently expressed vWF cleaving activity of the prepared C-terminal deletion variant by SDS-PAGE under reducing conditions.
Figure 4:
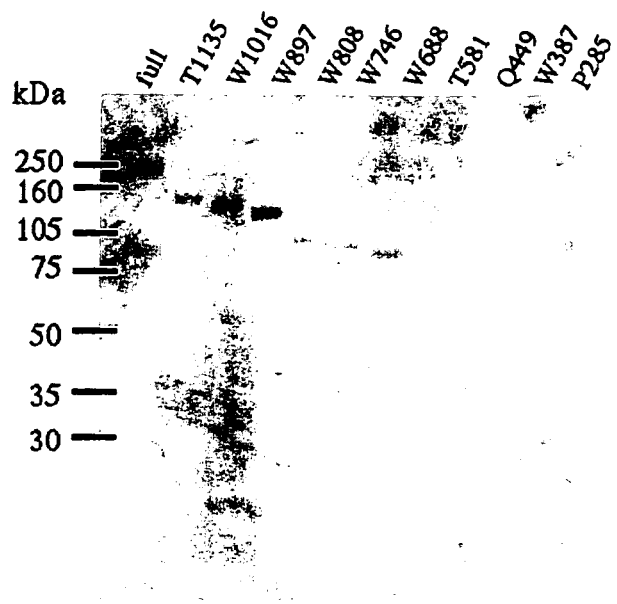
FIG. 4 shows Western blotting under non-reducing conditions giving the result demonstrating the epitope of PoAb1.

Consequently, as shown in FIG. 3, vWF cleaving activity was clearly recognized from the full-length molecule to W688stop molecule. In addition, when the expression pattern by the anti-FLAG antibody into the supernatant as described above was taken into consideration, in which expression by T581stop was not recognized into the supernatant, it was confirmed that disorder in secretion may be caused by cleavage near this region (from a Cys-rich region to the spacer domain) and therefore it was understood that it is important to include this domain in order to maintain the activity of this enzyme.

EXAMPLE 5

Analysis of Epitope of the Antibody Using Western Blotting

In order to identify the recognition regions for the established polyclonal antibodies (PoAb1 and PoAb2) on which Western blotting was performed following a conventional method and several monoclonal antibodies in which recognition sites were not considered to be competitive with each other (Clone No. WH10 (FERM BP-8174) previously prepared by the present inventors as well as WH63.1 (FERM BP-8175), WHS40.3 (FERM BP-8176) and Pep4-34.1 (FERM BP-8177)), Western blotting was performed utilizing transient expression culture supernatant of the partially deleted modified molecule of Example 4 (FIGS. 4 to 9).

Figure 5:
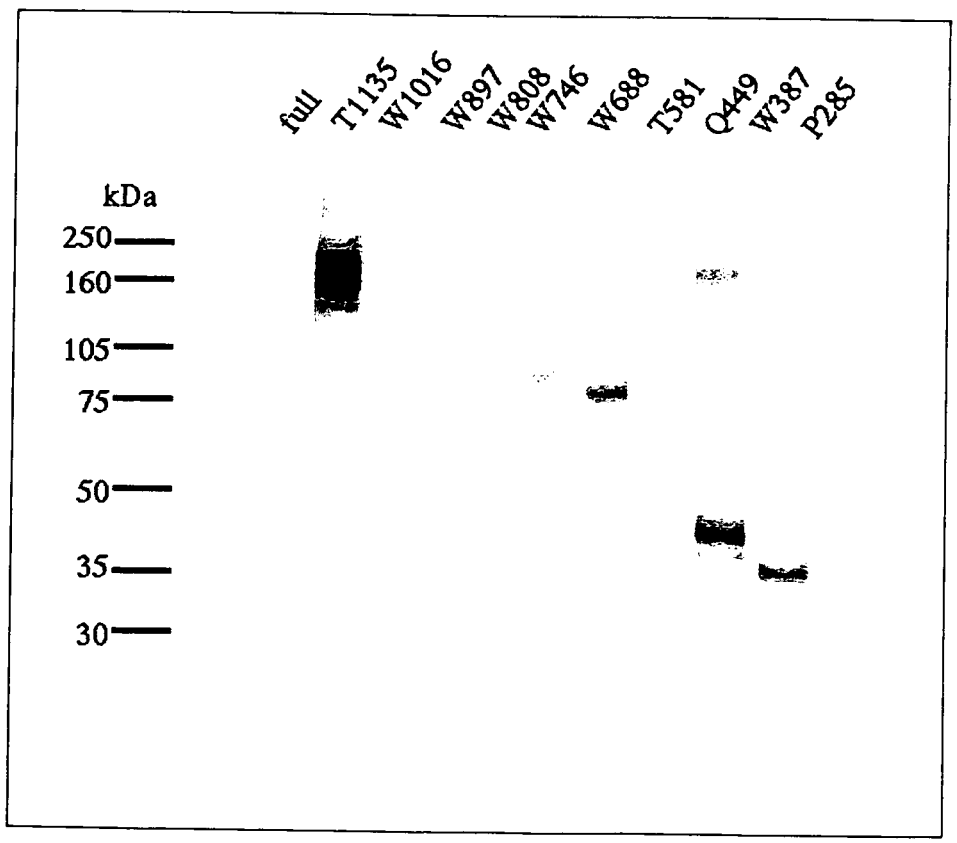
FIG. 5 shows Western blotting under non-reducing conditions giving the result demonstrating the epitope of PoAb2.
Figure 6:
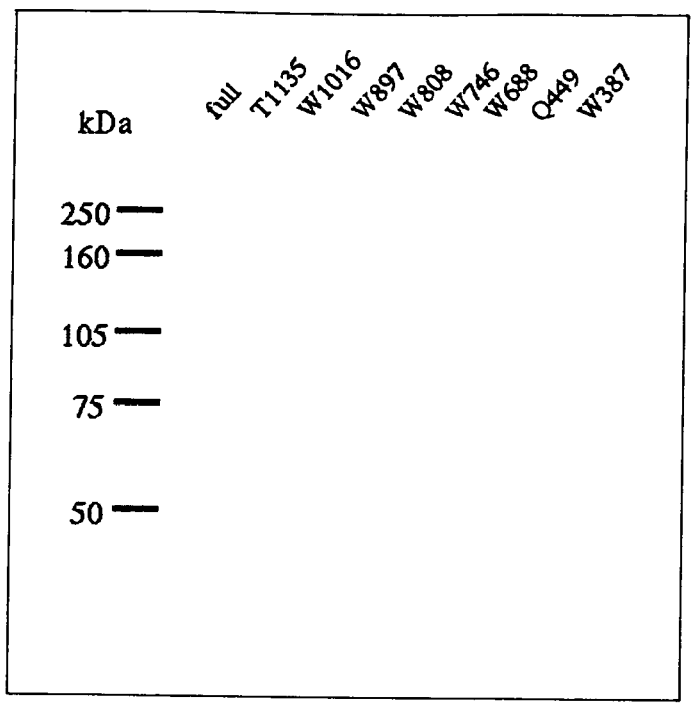
FIG. 6 shows Western blotting under non-reducing conditions giving the result demonstrating the epitope of MoAb Pep 4-34-1.
Figure 7:
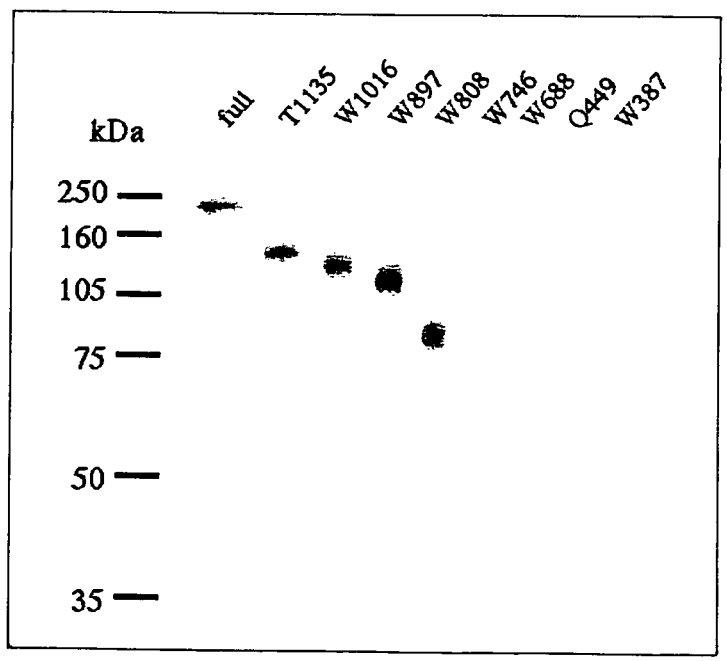
FIG. 7 shows Western blotting under non-reducing conditions giving the result demonstrating the epitope of MoAb WH10.
Figure 8:
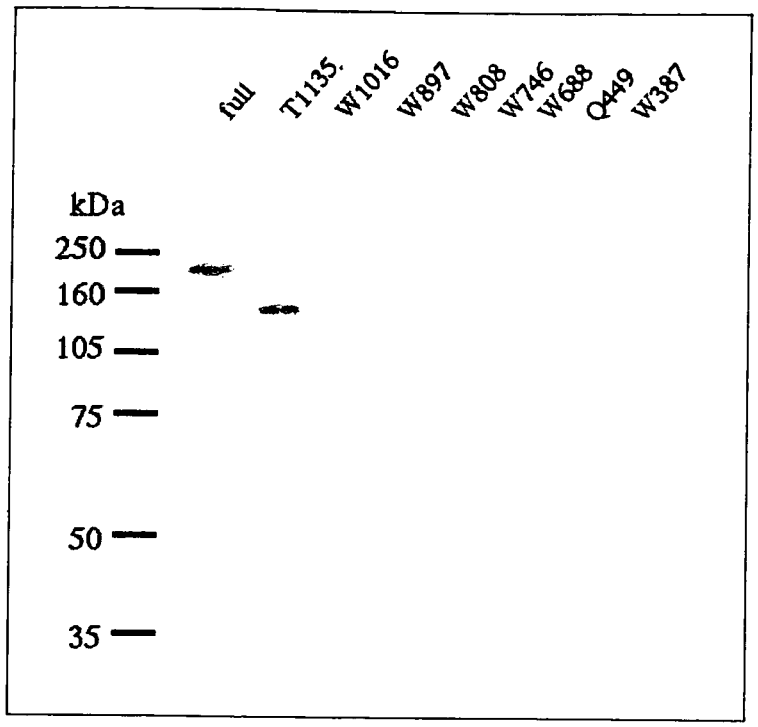
FIG. 8 shows Western blotting under non-reducing conditions giving the result demonstrating the epitope of MoAb WH63-1.
Figure 9:
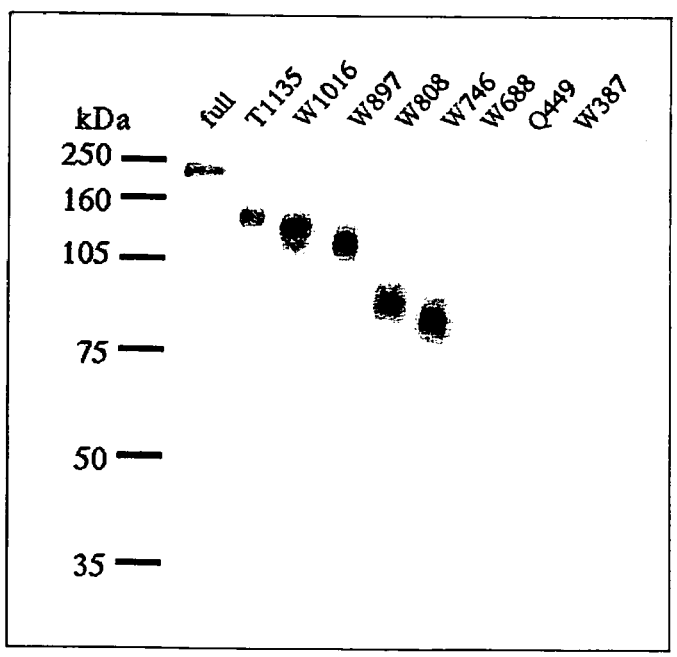
FIG. 9 shows Western blotting under non-reducing conditions giving the result demonstrating the epitope of MoAb WHS 40-3.

In addition to these, as for newly established clones WH2-22-1A (FERM BP-8483), WH2-1-1 (FERM BP-8484), WH2-11-1 (FERM BP-8485), Pep6-6A (FERM BP-8474) and Pep4-5B-1 (FERM BP-8475), similar analysis was performed. The recognition regions and the regions considered to be important for activity expression of the antibody are summarized in FIG. 10. It is presumed from FIG. 4 that the recognition region of PoAb1 extends from Q449stop to W688stop or over the full-length and considering the facts in combination that PoAb2 recognizes from P285stop to W387stop and to Tsp1—therefrom as is shown in FIG. 5, that the present polyclonal antibody PoAb1 has a neutralizing activity (described below) and that PoAb2 as well as PoAb3 also neutralized the enzyme activity of ADAMTS-13. It was confirmed that the region from the spacer domain to the N-terminus, metalloprotease domain, disintegrin-like domain, Tsp1-1 domain or Cys-Spacer region are functionally important in the in vitro assay and they may become a neutralizing region.

EXAMPLE 6

Identification of the Epitope Region of Anti-ADAMTS-13 Antibody Using ELISA

After 100 μL of anti-FLAG antibody was immobilized on an Immunomodule 96 well plate in 10 μg/mL, ADAMTS-13 wild type or the various above-mentioned deletion variants in which FLAG was appended to the polypeptide chain were immobilized, or alternatively variants of ADAMTS-13 were immobilized directly to a plate, and after 100 μL of suitably diluted MoAb was reacted to the plate for which a blocking operation was performed by a well-known method, the plate was washed with a buffer containing surfactant such as Tween, and after reacted with an anti-mouse IgHRP conjugated at 37° C. for 1 hour, washed and allowed to develop color by TMBZ, thereby the epitope region was searched in a similar way as in Example 5. Consequently, the result shown in the Example 5 was supported. In addition, it was confirmed that this method was effective in the detection and epitope analysis of the anti-ADAMTS-13 antibody which exists in human plasma.

EXAMPLE 7

Figure 11:
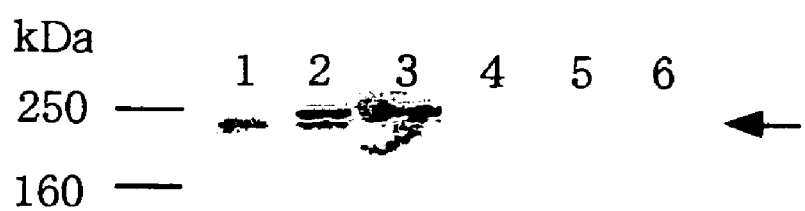
FIG. 11 shows the result of Western blotting under reducing conditions demonstrating ADAMTS-13 in the plasma from healthy people and TTP patients by means of the rabbit anti-serum obtained by immunizing with a partial peptide of ADAMTS-13.

Detection of ADAMTS-13 in Human Plasma by Western Blotting Using the Established Antibody Subsequently, using the antibodies prepared by the above-mentioned various methods, detection of the enzyme of the present invention was performed by the Western blotting method following a conventional method (such as Current Protocols in Molecular Biology: Chapter 10 analysis of proteins and Chapter 11 immunology). Detection was attempted in plasmas from healthy people and TTP patients under reduction condition by a peptide antibody obtained by using as an immunogen a peptide sequence of the C-terminus region of ADAMTS-13 (SEQ ID No. 2) Phe-Ser-Pro-Ala-Pro-Gln-Pro-Arg-Arg-Leu-Leu-Pro-Gly-Pro-Gln-Glu-Asn-Ser-Val-Gln-Ser-Ser connected to KLH, and although it was not clear for some plasmas from TTP patient, the band assumed to be the signal derived from ADAMTS-13 having generally about 250 kDa was confirmed (FIG. 11).

EXAMPLE 8

Figure 10:
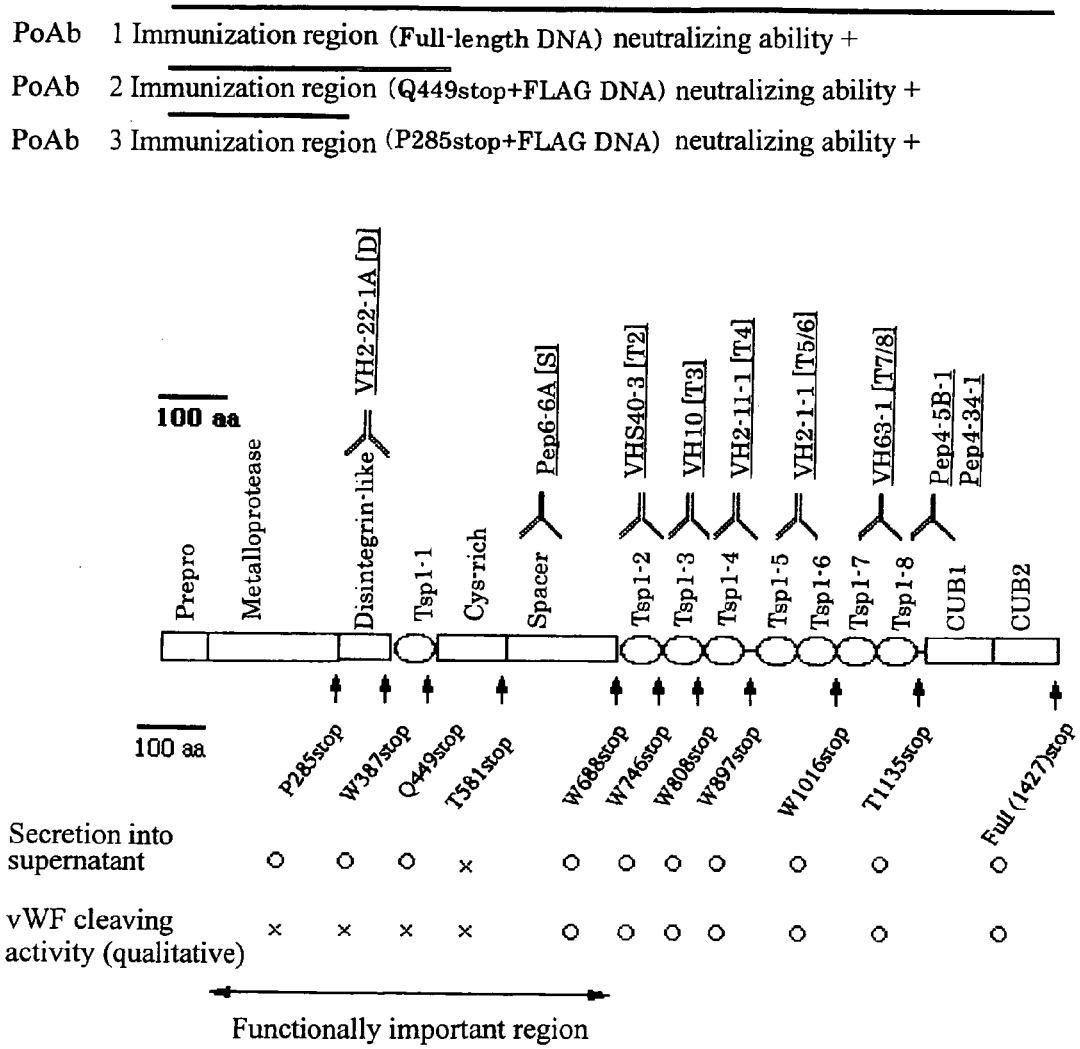
FIG. 10 summarizes the recognition regions and the domains important for activity expression of various antibodies.

Detection and Determination 1 of ADAMTS-13 in the Human Plasma by Enzyme-linked Immunosorbent Assay Using an Established Antibody The quantification of the present enzyme in various samples was performed using enzyme-linked immunosorbent assay (ELISA) constructed by a combination of an obtained polyclonal antibody and a monoclonal antibody (system of MoAb-PoAb)(FIG. 12)(as for the recognition epitope, see FIG. 10). The steps of the assay process are shown below:
1. Allow each reagent to be warmed to room temperature.
2. Add a sample to WH10 MoAb immobilized plate by 100 μL/well, 37° C., 1 hour.
3. Wash the plate with 0.05% Tween-20-TBS three times.
4. Dilute PoAb 1 or PoAb 2 with a diluting solution (1% BSA-TBS) so that it may become 1 μg/ml and add to the plate by 100 μL/well, 37° C., 1 hour.
5. Wash the plate with 0.05% Tween-20-TBS three times.
6. Dilute an anti-rabbit IgG-HRP labelled conjugate with a diluting solution (1% BSA-TBS) to 10000-fold and add to the plate by 100 μL/well, 37° C., 1 hour
7. Wash the plate with 0.05% Tween-20-TBS three times.
8. Add a TMB substrate solution (prepared by mixing two liquids at room temperature immediately before use) to the plate by 100 μL/well (positive well turns blue); add a reaction terminating liquid (0.5 M sulfuric acid) to the plate by 100 μL/well in about 10 minutes (so that the color of 100 ng/ml of the recombinant product enclosed as a standard may be finally about 1 as OD450 nm after the reaction is terminated) at room temperature (positive well turns yellow).
9. Measure the plate with a plate reader at 450 nm and 650 nm.

Figure 13:
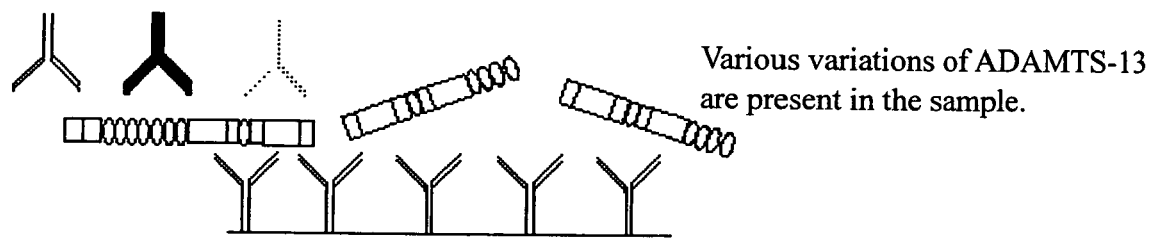
FIG. 13 is a conceptual figure of the ELISA method constructed by the antibodies prepared for each domain.

The standard used for quantification was one obtained by affinity purification of recombinant ADAMTS-13 by the antibody described below. Consequently, it was revealed that the concentration of ADAMTS-13 in the plasma of a healthy subject varies depending on the antibody used, which suggests that the present enzyme exists in various molecular forms in the plasma (Table 1). It was considered from this that as an ideal ELISA system, construction of a system utilizing a group of antibodies recognizing each domain and enabling decomposition pattern to be positively analyzed or a system hardly susceptible to these based on PoAb-PoAb (biotinylated PoAb-streptavidin HRP wherein PoAb purified with Protein G etc. is directly immobilized on an ELISA plate) shown in Table 2 was preferable (FIG. 13). In the system shown in FIG. 13, a polyclonal antibody (PoAb) or a monoclonal antibody (MoAb) having a recognition epitope toward the N-terminus (such as metalloprotease domain) is immobilized and MoAbs each having an epitope different for each domain as the secondary antibody on the detection side, thereby all the variations of ADAMTS-13 are trapped. Alternatively, MoAbs having such a wide variety of epitopes may be immobilized or a sandwich ELISA with PoAb and PoAb etc. is envisaged. It is possible in these systems to observe the correlation between pathologic condition and form of molecule existing in the plasma.

TABLE 1

|  | MoAb(WH10)-PoAb1 | MoAb(WH10)-PoAb2 |
| --- | --- | --- |
| Plasma 1 | 0.39 μg/ml | 1.2 μg/ml |
| Plasma 2 | 0.27 μg/ml | 1.1 μg/ml |
| Plasma 3 | 0.25 μg/ml | 0.9 μg/ml |
| TTPplasma | 0 μg/ml | 0 μg/ml |

TABLE 2

|  | PoAb1—PoAb1 |
| --- | --- |
| Plasma 4 | 1.0 μg/ml |
| Plasma 5 | 1.0 μg/ml |
| Plasma 6 | 0.9 μg/ml |

TABLE 2-continued

|  | PoAb1—PoAb1 |
| --- | --- |
| Plasma 7 | 1.1 μg/ml |
| Plasma 8 | 0.9 μg/ml |
| Plasma 9 | 0.8 μg/ml |

EXAMPLE 9

Detection and Determination 2 of ADAMTS-13 in the Human Plasma by Enzyme-linked Immunosorbent Assay Using an Established Antibody The quantification of the present enzyme in human plasma for several samples was performed using enzyme-linked immunosorbent assay constructed by a combination of obtained monoclonal antibodies (MoAb-MoAb system) (FIG. 14). The steps of the assay process are shown below:
1. Allow each reagent to be warmed to room temperature.
2. Add a sample to WH10 MoAb immobilized plate by 100 μL/well, 37° C., 1 hour
3. Wash the plate with 0.05% Tween-20-TBS three times.
4. Dilute a biotinized antibody with a diluting solution (1% BSA-TBS) so that it may become 1 μg/ml and add to the plate by 100 μL/well, 37° C., 1 hour.
5. Wash the plate with 0.05% Tween-20-TBS three times.
6. Dilute a streptavidin-HRP labelled conjugate with a diluting solution (1% BSA-TBS) to 10000-fold and add to the plate by 100 μL/well, 37° C., 1 hour
7. Wash the plate with 0.05% Tween-20-TBS three times.
8. Add a TMB substrate solution (prepared by mixing two liquids at room temperature immediately before use) to the plate by 100 μL/well (positive well turns blue); add a reaction terminating liquid (0.5 M sulfuric acid) to the plate by 100 μL/well in about 10 minutes (so that the color of 100 ng/ml of the recombinant product enclosed as a standard may be finally about 1 as OD450 nm after the reaction is terminated) at room temperature (positive well turns yellow).
9. Measure the plate with a plate reader at 450 nm and 650 nm.

As compared with the result of the above-mentioned Example 5, the system of this combination showed the lowest quantitative value (Table 3). In addition, the present enzyme purified from FI paste of human pooled plasma mentioned below was not detectable in this combination. This shows the importance of construction of various systems in which combination of antibodies is varied (FIG. 13) considering the fact that quantitative values change depending on the combination of antibodies.

TABLE 3

|  | MoAb(WH10)-PoAb1 | MoAb(WH10)-PoAb2 | MoAb(WH10)-MoAb(WH63-1) |
| --- | --- | --- | --- |
| Plasma 1 | 0.39 μg/ml | 1.2 μg/ml | 0.13 μg/ml |
| Plasma 2 | 0.27 μg/ml | 1.1 μg/ml | 0.09 μg/ml |
| Plasma 3 | 0.25 μg/ml | 0.9 μg/ml | 0.09 μg/ml |
| TTPplasma | 0 μg/ml | 0 μg/ml | 0 μg/ml |

EXAMPLE 10

Expression of Recombinant ADAMTS-13

A cell line stably expressing ADAMTS-13 was created by the following method (WO 02/088366) using 293-cell, a human embryo kidney cell line. As an outline, transfection was carried out in the following procedures. First, cells were seeded at 1-3×10$^5$ cells/35 mm dish, and the next day, the above-mentioned expression vector was added by 2 µg to 10 µl of TransIT (product of TAKARA) which is a polyamine transfection reagent and added to 200 µl of serum-free culture medium such as Opti-MEM, and a complex with DNA was prepared according to the instructions appended to the reagent, dropped onto the above-mentioned various cells prepared, incubated for 6 hours, and then the culture medium was exchanged and in further three days, the medium was exchanged to G418 added selection culture medium. The culture medium was exchanged in further three days, and expression clones (Clone No. VWFCP-293-35 and 293-2-4) were established from the selected colony group using limiting dilution method and the above-mentioned ELISA system of MoAb(WH10)-PoAb1.

EXAMPLE 11

Figure 15:
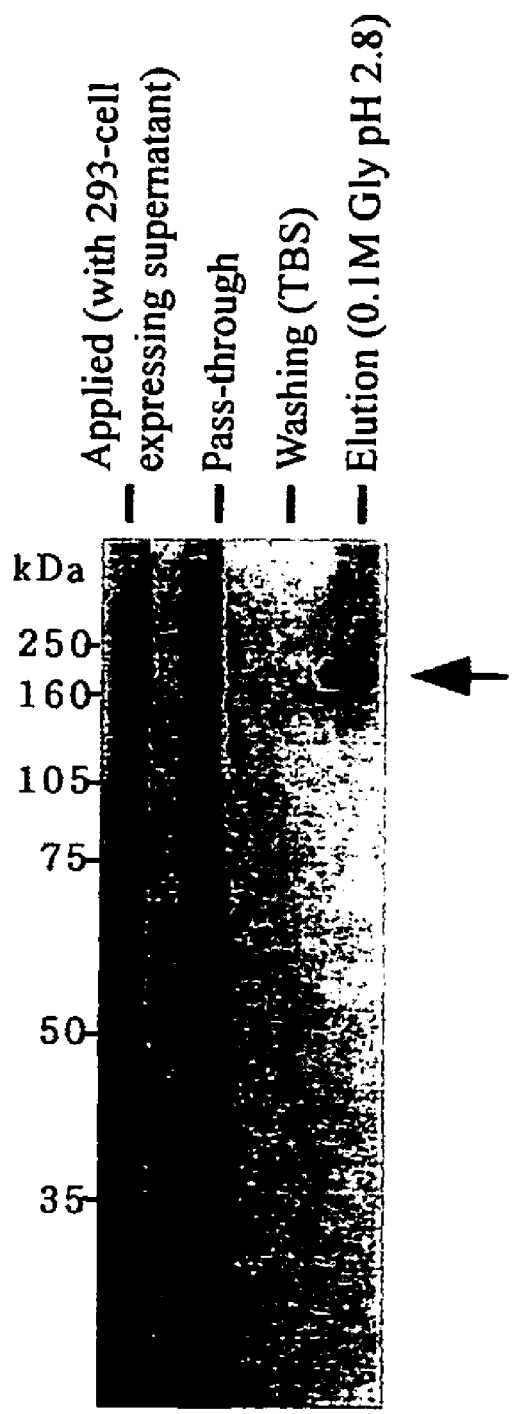
FIG. 15 is the electrophoresis profile of SDS-PAGE of recombinant ADAMTS-13 purified by affinity purification with the antibody column from the culture medium using human embryo kidney cell line 293 as a host.

Purification of Recombinant ADAMTS-13 from Culture Supernatant of the Recombinants Using Antibody An example is illustrated using WH10 as an example of the obtained antibody. An affinity column was prepared by binding this antibody to a suitable immobilization carrier, and used for purification of the enzyme. In the preparation of the affinity column, the antibody was immobilized using NHS activated Cellulofine manufactured by Chisso Corp. according to the appended instructions. About 1 ml of the thus prepared swollen carrier was used and after applied with the expression culture supernatant of the recombinant enzyme obtained by using as a host the 293-cell shown in Example 9, the column was washed with 50 mM Tris-HCl 0.1 M NaCl pH 7.5 (hereinafter, TBS) and eluted with 0.1 M glycine pH 3 buffer. The eluted fraction was neutralized with 1 M Tris-HCl pH 8.5, and dialyzed against TBS. SDS-PAGE of the obtained purified enzyme is shown in FIG. 15. It was also confirmed that the vWF cleaving activity exists in the obtained purified fraction. And it was confirmed from N-terminal amino acid sequence analysis of the fragment that the cleaved point of vWF fragmented with this recombinant enzyme is the position of 842Tyr-843Met.

Then, the partial amino acid sequence of ADAMTS-13 derived from the purified recombinant was determined. After SDS-PAGE, transferring to the PVDF membrane was effected by conventional method, and air-dried membrane was analyzed by Auto Protein Sequencer 492 manufactured by PE Applied Biosystems Co. Consequently, it was revealed that there is contained Ala-Ala-Gly-Gly-Ile- (SEQ ID NO: 24) as a partial N-terminus sequence. This sequence agreed with the N-terminus sequence of the matured enzyme presumed from gene structure.

EXAMPLE 12

Purification of ADAMTS-13 from FI Paste Derived from Pooled Human Plasma Using Antibody Solubilization of FI Paste FI paste was divided into portions of 12 g and stored in a frozen state. They were brought to 4° C. and thawed on the day before use, and the next day, 120 mL of a solubilizing buffer (0.05% Azide, 50 mM Tris-HCl pH 7.4, 100 mM NaCl) was added so that it might be 10 mg/mL and agitated at 37° C. for 2 hours. After carrying out cetrifugation at 10000 rpm for 10 minutes, supernatant was collected and filtered through a prefilter, 5.0-µm filter and 0.8-µm filter in this order to obtain a solubilized sample.

Gel Filtration Chromatography of ADAMTS-13

The solubilized FI paste was subjected to 1st gel filtration over Sephacryl S-300HR 5×90 cm column (Amersham-Pharmacia). 0.05% Azide, 50 mM Tris-HCl pH 7.4, 100 mM NaCl, which is the same as the solubilizing buffer (hereinafter, elution buffer) was used at a flow rate of 5 mL/min and a fraction corresponding to a presumed molecular weight of 100 k to 300 kDa was pooled, and a saturated ammonium sulfate solution was dropped as small portions to the final concentration equivalent to 33% saturation. This was further allowed to stand still at 4° C. overnight. Centrifugation was carried out at 10000 rpm for 10 minutes and the target active fraction was collected as precipitate on the next day. This procedure of solubilization, gel filtration and precipitation with ammonium sulfate was carried out for 5 batches and the product was stored in a frozen state at −20° C.

Two to three batches of precipitate obtained by ammonium sulfate precipitation of the 1st gel filtrate were dissolved in 50 mL of the elution buffer and passed through the Sephacryl S-300HR column (5×90 cm) in the same way as in the 1st time to conduct the 2nd gel filtration. The elution buffer, conditions and operation were the same as those of the 1 st time. This operation was carried out twice.

Figure 16:
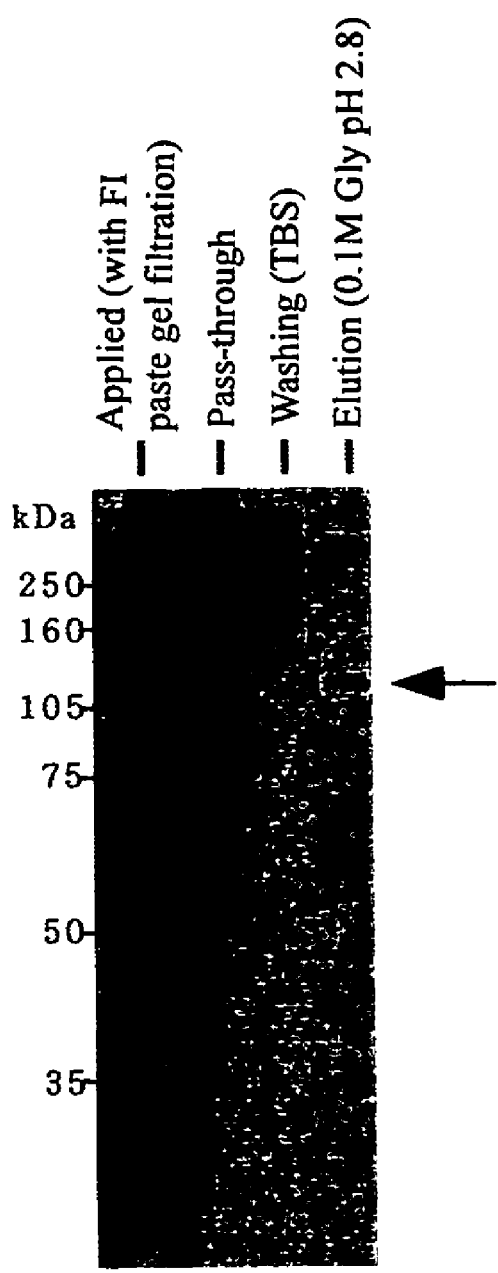
FIG. 16 is the electrophoresis profile of SDS-PAGE of ADAMTS-13 purified by affinity purification with the antibody column from FI paste of human pooled plasma.

Two batches of precipitate obtained by ammonium sulfate precipitation of the 2nd gel filtrate were dissolved in 50 mL of the elution buffer and passed through the Sephacryl S-300HR column (5×90 cm) in the same way as in the 1st and 2nd times to conduct the 3rd gel filtration. The elution buffer, conditions and operation were the same as those of the 1st and 2nd times. A fraction corresponding to a presumed molecular weight of 100 k to 300 kDa was pooled. This pooled sample was purified by the same procedure as in the above-mentioned recombinant ADAMTS-13 purification using a Clone No. WH10 monoclonal-antibody immobilized column. Consequently, almost single ADAMTS-13 having a size of 105 kDa to 160 kDa in SDS-PAGE as shown in FIG. 16 was purified. The N-terminal amino acid sequence of this was analyzed and the same result as the recombinant was obtained.

EXAMPLE 13

Neutralization of the Present Enzyme Activity by Antibody

The neutralizing activity of the vWF cleaving enzyme by the above-mentioned rabbit polyclonal antibody was evaluated. A normal rabbit serum, a rabbit antiserum obtained by using as an immunogen the peptide sequence (SEQ ID No. 2) Phe-Ser-Pro-Ala-Pro-Gln-Pro-Arg-Arg-Leu-Leu-Pro-Gly-Pro-Gln-Glu-Asn-Ser-Val-Gln-Ser-Ser of the C-terminus region connected to KLH and an antiserum (PoAb1)

immuno-derived by a protein expressed by the full-length ADAMTS-13 expression vector each diluted to 1:1 or 1:10 times by volume were reacted with 1 to 10 µg/ml (estimated by Bradford method) of the recombinant ADAMTS-13 at a ratio of 1 to 1 at 37° C. for 1 hour beforehand and the antisera were subjected to the assay of the vWF cleaving activity mentioned above to estimate the inhibition in the activity thereof.

As a result, those having an inhibitory activity of the present enzyme were prepared as shown in FIG. 17 (EDTA, an inhibitor of metalloprotease, was used as a positive control of the inhibition). In addition, it was guessed from the result of the epitope analysis of the polyclonal antibody (PoAb1) having a neutralizing activity (FIG. 4) that a neutralization epitope might exist toward the N-terminus from the spacer domain in the domain structure of ADAMTS-13. Furthermore, it was confirmed that PoAb2 and PoAb3 also had neutralizing ability. From these, metalloprotease domain, disintegrin-like domain, etc. were assumed as a domain having a capability of neutralization. The fact that a neutralizing antibody can be thus created suggests that an acquired TTP patient-like model who has autoantibody against ADAMTS-13 can be also constructed.

EXAMPLE 14

Detection of Anti-ADAMTS-13 Antibody in Human Plasma

Figure 18:
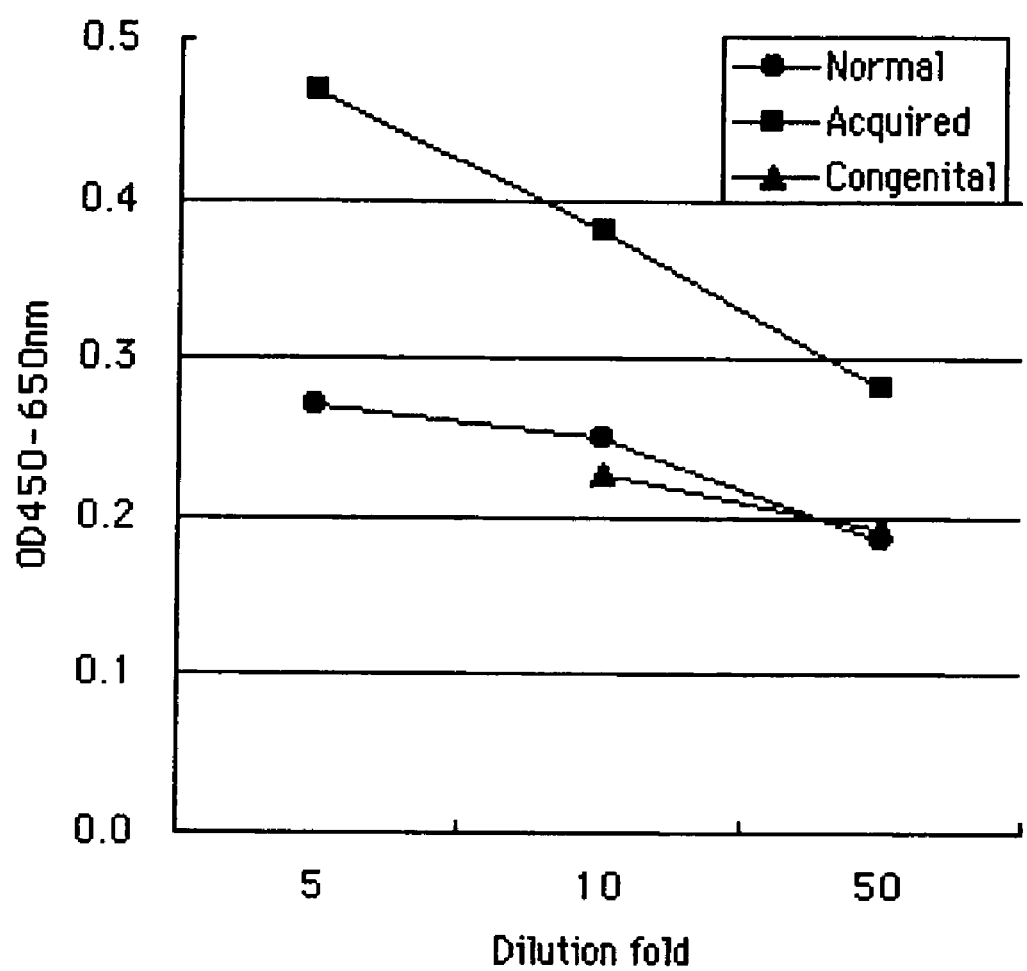
FIG. 18 shows detection (ELISA method) of anti-ADAMTS-13 antibody in the plasma of a patient with acquired TTP.

The method shown in Example 6 was used, and detection of anti-ADAMTS-13 antibody in the plasma of an acquired TTP patient was attempted. After 100 µL of anti-FLAG antibody was immobilized on an Immunomodule 96 well plate in 2 µg/mL, FLAG tagged ADAMTS-13 wild type was reacted. After that, 100 µL of a sample plasma diluted to 5, 10, 50 times was reacted at 37° C. for 1 hour, the plate was washed with a Tris-buffer containing 0.05% of Tween20, and after reacted with an anti-human IgHRP conjugated at 37° C. for 1 hour, washed, allowed to develop color by TMBZ etc. As a result, it was confirmed as shown in FIG. 18, that only the plasma of an acquired TTP patient (Acquired) exhibited a significant value in the absorption at 450 nm as compared with a normal plasma (Normal) and a congenital TTP plasma (Congenital) and had anti-ADAMTS-13 antibody.

EXAMPLE 15

Production of an Anti-mouse ADAMTS-13 Polyclonal Antibody (PoAb)

Figure 19:
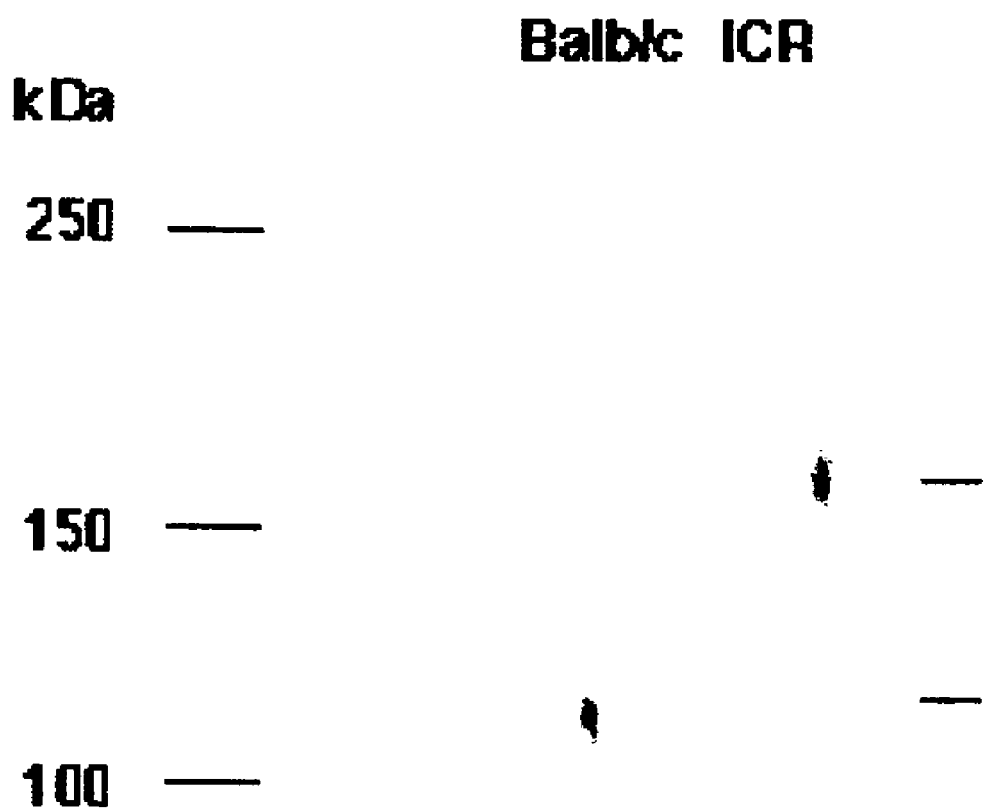
FIG. 19 shows detection of ADAMTS-13 in the plasma of a mouse (Western blotting method).

In the similar manner as in human, an expression vector into which a gene encoding the present enzyme of mouse (WO 02/088366) was introduced was transfected to a rabbit subcutaneously, intradermically or intramuscularly according to a conventional method to create polyclonal antibodies (PoAb). Using the obtained antibody, the present enzyme was immunoprecipitated from the mouse plasma and detected (FIG. 19). It was recognized that the molecular size of the present enzyme changed depending on the mouse line. Moreover, this polyclonal antibody was solid phased on a plate and further biotinylated to construct a sandwich ELISA with PoAb and PoAb (Table 4). Thereby, measurement of blood level of the present enzyme can be assayed even in mouse.

TABLE 4

| 450 nm-650 nm value | ×5 | ×10 | ×20 | ×40 | Buffer(Blank) |
|---|---|---|---|---|---|
| Concentrated supernatant in which the recombinant expresses | 0.809 | 0.554 | 0.341 | | 0.087 |
| Balb/c plasma | | | 0.257 | 0.180 | |
| ICR plasma | | | 0.375 | 0.279 | |

As for all the publications cited in this specification, the entire contents thereof are incorporated in this specification. In addition, it will be easily understood by those skilled in the art that various modifications and changes to the present invention can be effected without deviating from the technical idea and the scope of the invention described in the appended claims. It is intended that the present invention also includes such modifications and changes.

INDUSTRIAL APPLICABILITY

The antibody of the present invention shows specific immunoreactivity to ADAMTS-13. Therefore, rapid detection of the amount of ADAMTS-13 enzyme, diagnosis of the diseases associated with changes of the present enzyme, efficient purification of ADAMTS-13, or neutralization of the enzyme activity of ADAMTS-13 is enabled. Thus, the antibody of the present invention also has various applications including detection and purification of ADAMTS-13. The antibody of the present invention thus useful can be obtained in a desired amount easily by the process for preparing the antibody of the present invention.

The present invention exhibits the thus remarkable action and effect and can be said as an invention making a great contribution to the art. In addition, ADAMTS-13 partial deletion variant of the present invention can also be used for the determination of functionally important domain etc. Furthermore, the judgment of the existence or non-existence of the antibody against the present enzyme in the sample using these enzyme molecules is enabled, and the means for further detailed research on the cause of thrombocytopenia is provided, thereby the risk of inadvertently erroneous blood platelet injection is made avoidable.

---

The invention claimed is:

1. An isolated monoclonal antibody produced by a hybridoma selected from the group consisting of hybridoma line WHIO (accession number FERM BP-08174), hybridoma line WH63.1 (accession number FERM BP-08175), hybridoma line WHS40.3 (accession number FERM BP-08176), hybridoma line Pep4H 34.1 (accession number FERM BP-08177), hybridoma line WH2-22-1A (accession number FERM BP-08483), hybridoma line WH2-1-1 (accession number FERM BP-08484), hybridoma line WH2-11-1 (accession number FERM BP-08485), hybridoma line Pep6-6A (accession number FERM BP-08474) and hybridoma line PEP4-5B-1 (accession number FERM BP-08475).

2. A composition comprising a monoclonal antibody according to claim 1.

3. A hybridoma that is selected from the group consisting of hybridoma line WHIO (accession number FERM BP-08174), hybridoma line WH63.1 (accession number FERM BP-08175), hybridoma line WHS40.3 (accession number FERM BP-08176), hybridoma line Pep4-34.1 (accession number FERM BP-08177), hybridoma line WH2-22-1A (accession number FERM BP-08483), hybridoma line WH2-1-1 (accession number FERM BP-08484), hybridoma line WH2-11-1 (accession number FERM BP08485), hybridoma line Pep6-6A (accession number FERM BP-08474) and hybridoma line Pep4-5B-1 (accession number FERM BP-08475).

4. An immunoassay kit comprising an antibody according to claim 1.

5. method for detecting ADAMTS-13, comprising contacting a monoclonal antibody according to claim 1 with a biological sample and detecting ADAMTS-13 by immunoreaction.

6. The detection method according to claim 5, wherein said immunoreaction is a radioimmunoassay, an enzyme immunoassay or a fluoroimmunoassay.

7. The detection method according to claims 5, wherein the biological sample is extracted from a living body.

8. The detection method according to claims 6, wherein the biological sample is extracted from a living body.

* * * * *

UNITED STATES PATENT AND TRADEMARK OFFICE
CERTIFICATE OF CORRECTION

PATENT NO.        : 7,575,872 B2                                     Page 1 of 1
APPLICATION NO. : 10/529009
DATED             : August 18, 2009
INVENTOR(S)       : Soejima et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 583 days.

Signed and Sealed this

Seventh Day of September, 2010

David J. Kappos
*Director of the United States Patent and Trademark Office*

SEQUENCE LISTING

<160> NUMBER OF SEQ ID NOS: 20

<210> SEQ ID NO 1
<211> LENGTH: 1427
<212> TYPE: PRT
<213> ORGANISM: Homo sapiens

<400> SEQUENCE: 1

-continued

```
Met His Gln Arg His Pro Arg Ala Arg Cys Pro Pro Leu Cys Val
1               5                   10                  15

Ala Gly Ile Leu Ala Cys Gly Phe Leu Leu Gly Cys Trp Gly Pro
                20                  25                  30

Ser His Phe Gln Gln Ser Cys Leu Gln Ala Leu Glu Pro Gln Ala
                35                  40                  45

Val Ser Ser Tyr Leu Ser Pro Gly Ala Pro Leu Lys Gly Arg Pro
                50                  55                  60

Pro Ser Pro Gly Phe Gln Arg Gln Arg Gln Arg Gln Arg Arg Ala
                65                  70                  75

Ala Gly Gly Ile Leu His Leu Glu Leu Leu Val Ala Val Gly Pro
                80                  85                  90

Asp Val Phe Gln Ala His Gln Glu Asp Thr Glu Arg Tyr Val Leu
                95                  100                 105

Thr Asn Leu Asn Ile Gly Ala Glu Leu Leu Arg Asp Pro Ser Leu
                110                 115                 120

Gly Ala Gln Phe Arg Val His Leu Val Lys Met Val Ile Leu Thr
                125                 130                 135

Glu Pro Glu Gly Ala Pro Asn Ile Thr Ala Asn Leu Thr Ser Ser
                140                 145                 150

Leu Leu Ser Val Cys Gly Trp Ser Gln Thr Ile Asn Pro Glu Asp
                155                 160                 165

Asp Thr Asp Pro Gly His Ala Asp Leu Val Leu Tyr Ile Thr Arg
                170                 175                 180

Phe Asp Leu Glu Leu Pro Asp Gly Asn Arg Gln Val Arg Gly Val
                185                 190                 195

Thr Gln Leu Gly Gly Ala Cys Ser Pro Thr Trp Ser Cys Leu Ile
                200                 205                 210

Thr Glu Asp Thr Gly Phe Asp Leu Gly Val Thr Ile Ala His Glu
                215                 220                 225

Ile Gly His Ser Phe Gly Leu Glu His Asp Gly Ala Pro Gly Ser
                230                 235                 240

Gly Cys Gly Pro Ser Gly His Val Met Ala Ser Asp Gly Ala Ala
                245                 250                 255

Pro Arg Ala Gly Leu Ala Trp Ser Pro Cys Ser Arg Arg Gln Leu
                260                 265                 270

Leu Ser Leu Leu Ser Ala Gly Arg Ala Arg Cys Val Trp Asp Pro
                275                 280                 285

Pro Arg Pro Gln Pro Gly Ser Ala Gly His Pro Pro Asp Ala Gln
                290                 295                 300

Pro Gly Leu Tyr Tyr Ser Ala Asn Glu Gln Cys Arg Val Ala Phe
                305                 310                 315

Gly Pro Lys Ala Val Ala Cys Thr Phe Ala Arg Glu His Leu Asp
                320                 325                 330

Met Cys Gln Ala Leu Ser Cys His Thr Asp Pro Leu Asp Gln Ser
                335                 340                 345

Ser Cys Ser Arg Leu Leu Val Pro Leu Leu Asp Gly Thr Glu Cys
                350                 355                 360

Gly Val Glu Lys Trp Cys Ser Lys Gly Arg Cys Arg Ser Leu Val
                365                 370                 375

Glu Leu Thr Pro Ile Ala Ala Val His Gly Arg Trp Ser Ser Trp
                380                 385                 390

Gly Pro Arg Ser Pro Cys Ser Arg Ser Cys Gly Gly Gly Val Val
```

-continued

```
                395                 400                 405
Thr Arg Arg Arg Gln Cys Asn Asn Pro Arg Pro Ala Phe Gly Gly
            410                 415                 420
Arg Ala Cys Val Gly Ala Asp Leu Gln Ala Glu Met Cys Asn Thr
            425                 430                 435
Gln Ala Cys Glu Lys Thr Gln Leu Glu Phe Met Ser Gln Gln Cys
            440                 445                 450
Ala Arg Thr Asp Gly Gln Pro Leu Arg Ser Ser Pro Gly Gly Ala
            455                 460                 465
Ser Phe Tyr His Trp Gly Ala Ala Val Pro His Ser Gln Gly Asp
            470                 475                 480
Ala Leu Cys Arg His Met Cys Arg Ala Ile Gly Glu Ser Phe Ile
            485                 490                 495
Met Lys Arg Gly Asp Ser Phe Leu Asp Gly Thr Arg Cys Met Pro
            500                 505                 510
Ser Gly Pro Arg Glu Asp Gly Thr Leu Ser Leu Cys Val Ser Gly
            515                 520                 525
Ser Cys Arg Thr Phe Gly Cys Asp Gly Arg Met Asp Ser Gln Gln
            530                 535                 540
Val Trp Asp Arg Cys Gln Val Cys Gly Gly Asp Asn Ser Thr Cys
            545                 550                 555
Ser Pro Arg Lys Gly Ser Phe Thr Ala Gly Arg Ala Arg Glu Tyr
            560                 565                 570
Val Thr Phe Leu Thr Val Thr Pro Asn Leu Thr Ser Val Tyr Ile
            575                 580                 585
Ala Asn His Arg Pro Leu Phe Thr His Leu Ala Val Arg Ile Gly
            590                 595                 600
Gly Arg Tyr Val Val Ala Gly Lys Met Ser Ile Ser Pro Asn Thr
            605                 610                 615
Thr Tyr Pro Ser Leu Leu Glu Asp Gly Arg Val Glu Tyr Arg Val
            620                 625                 630
Ala Leu Thr Glu Asp Arg Leu Pro Arg Leu Glu Glu Ile Arg Ile
            635                 640                 645
Trp Gly Pro Leu Gln Glu Asp Ala Asp Ile Gln Val Tyr Arg Arg
            650                 655                 660
Tyr Gly Glu Glu Tyr Gly Asn Leu Thr Arg Pro Asp Ile Thr Phe
            665                 670                 675
Thr Tyr Phe Gln Pro Lys Pro Arg Gln Ala Trp Val Trp Ala Ala
            680                 685                 690
Val Arg Gly Pro Cys Ser Val Ser Cys Gly Ala Gly Leu Arg Trp
            695                 700                 705
Val Asn Tyr Ser Cys Leu Asp Gln Ala Arg Lys Glu Leu Val Glu
            710                 715                 720
Thr Val Gln Cys Gln Gly Ser Gln Gln Pro Ala Trp Pro Glu
            725                 730                 735
Ala Cys Val Leu Glu Pro Cys Pro Pro Tyr Trp Ala Val Gly Asp
            740                 745                 750
Phe Gly Pro Cys Ser Ala Ser Cys Gly Gly Gly Leu Arg Glu Arg
            755                 760                 765
Pro Val Arg Cys Val Glu Ala Gln Gly Ser Leu Leu Lys Thr Leu
            770                 775                 780
Pro Pro Ala Arg Cys Arg Ala Gly Ala Gln Gln Pro Ala Val Ala
            785                 790                 795
```

-continued

Leu Glu Thr Cys Asn Pro Gln Pro Cys Pro Ala Arg Trp Glu Val
            800                 805                 810

Ser Glu Pro Ser Ser Cys Thr Ser Ala Gly Gly Ala Gly Leu Ala
            815                 820                 825

Leu Glu Asn Glu Thr Cys Val Pro Gly Ala Asp Gly Leu Glu Ala
            830                 835                 840

Pro Val Thr Glu Gly Pro Gly Ser Val Asp Glu Lys Leu Pro Ala
            845                 850                 855

Pro Glu Pro Cys Val Gly Met Ser Cys Pro Pro Gly Trp Gly His
            860                 865                 870

Leu Asp Ala Thr Ser Ala Gly Glu Lys Ala Pro Ser Pro Trp Gly
            875                 880                 885

Ser Ile Arg Thr Gly Ala Gln Ala Ala His Val Trp Thr Pro Ala
            890                 895                 900

Ala Gly Ser Cys Ser Val Ser Cys Gly Arg Gly Leu Met Glu Leu
            905                 910                 915

Arg Phe Leu Cys Met Asp Ser Ala Leu Arg Val Pro Val Gln Glu
            920                 925                 930

Glu Leu Cys Gly Leu Ala Ser Lys Pro Gly Ser Arg Arg Glu Val
            935                 940                 945

Cys Gln Ala Val Pro Cys Pro Ala Arg Trp Gln Tyr Lys Leu Ala
            950                 955                 960

Ala Cys Ser Val Ser Cys Gly Arg Gly Val Val Arg Arg Ile Leu
            965                 970                 975

Tyr Cys Ala Arg Ala His Gly Glu Asp Asp Gly Glu Glu Ile Leu
            980                 985                 990

Leu Asp Thr Gln Cys Gln Gly Leu Pro Arg Pro Glu Pro Gln Glu
            995                 1000                1005

Ala Cys Ser Leu Glu Pro Cys Pro Pro Arg Trp Lys Val Met Ser
            1010                1015                1020

Leu Gly Pro Cys Ser Ala Ser Cys Gly Leu Gly Thr Ala Arg Arg
            1025                1030                1035

Ser Val Ala Cys Val Gln Leu Asp Gln Gly Gln Asp Val Glu Val
            1040                1045                1050

Asp Glu Ala Ala Cys Ala Ala Leu Val Arg Pro Glu Ala Ser Val
            1055                1060                1065

Pro Cys Leu Ile Ala Asp Cys Thr Tyr Arg Trp His Val Gly Thr
            1070                1075                1080

Trp Met Glu Cys Ser Val Ser Cys Gly Asp Gly Ile Gln Arg Arg
            1085                1090                1095

Arg Asp Thr Cys Leu Gly Pro Gln Ala Gln Ala Pro Val Pro Ala
            1100                1105                1110

Asp Phe Cys Gln His Leu Pro Lys Pro Val Thr Val Arg Gly Cys
            1115                1120                1125

Trp Ala Gly Pro Cys Val Gly Gln Gly Thr Pro Ser Leu Val Pro
            1130                1135                1140

His Glu Glu Ala Ala Ala Pro Gly Arg Thr Thr Ala Thr Pro Ala
            1145                1150                1155

Gly Ala Ser Leu Glu Trp Ser Gln Ala Arg Gly Leu Leu Phe Ser
            1160                1165                1170

Pro Ala Pro Gln Pro Arg Arg Leu Leu Pro Gly Pro Gln Glu Asn
            1175                1180                1185

```
Ser Val Gln Ser Ser Ala Cys Gly Arg Gln His Leu Glu Pro Thr
            1190                1195                1200

Gly Thr Ile Asp Met Arg Gly Pro Gly Gln Ala Asp Cys Ala Val
            1205                1210                1215

Ala Ile Gly Arg Pro Leu Gly Glu Val Val Thr Leu Arg Val Leu
            1220                1225                1230

Glu Ser Ser Leu Asn Cys Ser Ala Gly Asp Met Leu Leu Leu Trp
            1235                1240                1245

Gly Arg Leu Thr Trp Arg Lys Met Cys Arg Lys Leu Leu Asp Met
            1250                1255                1260

Thr Phe Ser Ser Lys Thr Asn Thr Leu Val Val Arg Gln Arg Cys
            1265                1270                1275

Gly Arg Pro Gly Gly Gly Val Leu Leu Arg Tyr Gly Ser Gln Leu
            1280                1285                1290

Ala Pro Glu Thr Phe Tyr Arg Glu Cys Asp Met Gln Leu Phe Gly
            1295                1300                1305

Pro Trp Gly Glu Ile Val Ser Pro Ser Leu Ser Pro Ala Thr Ser
            1310                1315                1320

Asn Ala Gly Gly Cys Arg Leu Phe Ile Asn Val Ala Pro His Ala
            1325                1330                1335

Arg Ile Ala Ile His Ala Leu Ala Thr Asn Met Gly Ala Gly Thr
            1340                1345                1350

Glu Gly Ala Asn Ala Ser Tyr Ile Leu Ile Arg Asp Thr His Ser
            1355                1360                1365

Leu Arg Thr Thr Ala Phe His Gly Gln Gln Val Leu Tyr Trp Glu
            1370                1375                1380

Ser Glu Ser Ser Gln Ala Glu Met Glu Phe Ser Glu Gly Phe Leu
            1385                1390                1395

Lys Ala Gln Ala Ser Leu Arg Gly Gln Tyr Trp Thr Leu Gln Ser
            1400                1405                1410

Trp Val Pro Glu Met Gln Asp Pro Gln Ser Trp Lys Gly Lys Glu
            1415                1420                1425

Gly Thr

<210> SEQ ID NO 2
<211> LENGTH: 22
<212> TYPE: PRT
<213> ORGANISM: Homo sapiens

<400> SEQUENCE: 2

Phe Ser Pro Ala Pro Gln Pro Arg Arg Leu Leu Pro Gly Pro Gln
1               5                   10                  15

Glu Asn Ser Val Gln Ser Ser
                20

<210> SEQ ID NO 3
<211> LENGTH: 18
<212> TYPE: PRT
<213> ORGANISM: Homo sapiens

<400> SEQUENCE: 3

Asp Arg Leu Pro Arg Leu Glu Glu Ile Arg Ile Trp Gly Pro Leu
1               5                   10                  15

Gln Glu Asp

<210> SEQ ID NO 4
```

```
<211> LENGTH: 30
<212> TYPE: DNA
<213> ORGANISM: Homo sapiens

<400> SEQUENCE: 4
ctggagcacg acggcgcgcc cggcagcggc                              30

<210> SEQ ID NO 5
<211> LENGTH: 30
<212> TYPE: DNA
<213> ORGANISM: Homo sapiens

<400> SEQUENCE: 5
atgtgcaaca ctcaggcctg cgagaagacc                              30

<210> SEQ ID NO 6
<211> LENGTH: 30
<212> TYPE: DNA
<213> ORGANISM: Homo sapiens

<400> SEQUENCE: 6
ccaacctgac cagtgtctac attgccaacc                              30

<210> SEQ ID NO 7
<211> LENGTH: 21
<212> TYPE: DNA
<213> ORGANISM: Homo sapiens

<400> SEQUENCE: 7
ctggagccct gcccacctag g                                       21

<210> SEQ ID NO 8
<211> LENGTH: 62
<212> TYPE: DNA
<213> ORGANISM: Homo sapiens

<400> SEQUENCE: 8
tccgtcgact cttatcactt atcgtcatcg tccttgtagt cgtcccacac gcagcgcgcc   60
cg                                                            62

<210> SEQ ID NO 9
<211> LENGTH: 62
<212> TYPE: DNA
<213> ORGANISM: Homo sapiens

<400> SEQUENCE: 9
tccgtcgact cttatcactt atcgtcatcg tccttgtagt cgcgcccatg cactgctgct   60
at                                                            62

<210> SEQ ID NO 10
<211> LENGTH: 62
<212> TYPE: DNA
<213> ORGANISM: Homo sapiens

<400> SEQUENCE: 10
gccgtcgact cttatcactt atcgtcatcg tccttgtagt cttgcgacat gaactccagc   60
tg                                                            62

<210> SEQ ID NO 11
<211> LENGTH: 62
<212> TYPE: DNA
<213> ORGANISM: Homo sapiens
```

<400> SEQUENCE: 11
gccgtcgact cttatcactt atcgtcatcg tccttgtagt ccaggttggg ggtaactgtc    60
ag                                                                   62

<210> SEQ ID NO 12
<211> LENGTH: 62
<212> TYPE: DNA
<213> ORGANISM: Homo sapiens

<400> SEQUENCE: 12
tccgtcgact cttatcactt atcgtcatcg tccttgtagt ccacccaggc ctgccgtggc    60
tt                                                                   62

<210> SEQ ID NO 13
<211> LENGTH: 62
<212> TYPE: DNA
<213> ORGANISM: Homo sapiens

<400> SEQUENCE: 13
tccgtcgact cttatcactt atcgtcatcg tccttgtagt cgtagggagg gcagggttcg    60
ag                                                                   62

<210> SEQ ID NO 14
<211> LENGTH: 62
<212> TYPE: DNA
<213> ORGANISM: Homo sapiens

<400> SEQUENCE: 14
tccgtcgact cttatcactt atcgtcatcg tccttgtagt ccctggcagg gcagggctgg    60
gg                                                                   62

<210> SEQ ID NO 15
<211> LENGTH: 62
<212> TYPE: DNA
<213> ORGANISM: Homo sapiens

<400> SEQUENCE: 15
gccgtcgact cttatcactt atcgtcatcg tccttgtagt ccacgtgtgc agcttgagcc    60
cc                                                                   62

<210> SEQ ID NO 16
<211> LENGTH: 62
<212> TYPE: DNA
<213> ORGANISM: Homo sapiens

<400> SEQUENCE: 16
gccgtcgact cttatcactt atcgtcatcg tccttgtagt ccctaggtgg gcagggctcc    60
ag                                                                   62

<210> SEQ ID NO 17
<211> LENGTH: 62
<212> TYPE: DNA
<213> ORGANISM: Homo sapiens

<400> SEQUENCE: 17
gccgtcgact cttatcactt atcgtcatcg tccttgtagt cacccctgtcc cacacagggc    60 cc                                                                   62

```
<210> SEQ ID NO 18
<211> LENGTH: 60
<212> TYPE: DNA
<213> ORGANISM: Homo sapiens

<400> SEQUENCE: 18
tccaagcttg tcgactctta tcacttatcg tcatcgtcct tgtagtcggt tccttcctttt        60

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 19
gactacaagg acgatgacga taagtga                                             27

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence:Synthetic

<400> SEQUENCE: 20

Asp Tyr Lys Asp Asp Asp Asp Lys
1               5
```